US012569625B2

(12) United States Patent　　(10) Patent No.:　US 12,569,625 B2

Ducarouge　　(45) Date of Patent:　Mar. 10, 2026

(54) RIGID NEEDLE SHIELD REMOVER WITH DROP TEST FEATURE FOR AUTOINJECTOR

(71) Applicant: Becton Dickinson France, Le Pont-de-Claix (FR)

(72) Inventor: Pierre Ducarouge, Grenoble (FR)

(73) Assignee: Becton Dickinson France, Le Pont de Claix (FR)

( * ) Notice: Subject to any disclaimer, the term of this patent is extended or adjusted under 35 U.S.C. 154(b) by 983 days.

(21) Appl. No.: 17/426,050

(22) PCT Filed: Feb. 26, 2020

(86) PCT No.: PCT/EP2020/055011

§ 371 (c)(1),
　(2) Date: Jul. 27, 2021

(87) PCT Pub. No.: WO2020/173997

PCT Pub. Date: Sep. 3, 2020

(65) Prior Publication Data

US 2022/0111153 A1　　Apr. 14, 2022

(30) Foreign Application Priority Data

Feb. 26, 2019　(EP) ..................................... 19305229

(51) Int. Cl.
　*A61M 5/32*　　　(2006.01)
(52) U.S. Cl.
　CPC ................................. *A61M 5/3204* (2013.01)

(58) Field of Classification Search
　CPC .................................................. A61M 5/3204
　See application file for complete search history.

(56) References Cited

U.S. PATENT DOCUMENTS

| | | |
|---|---|---|
| 3,562,564 A | 2/1971 | Potter |
| 6,056,728 A | 5/2000 | von Schuckmann |
| 6,090,070 A | 7/2000 | Hager et al. |
| 6,183,446 B1 | 2/2001 | Jeanbourquin |
| 6,746,429 B2 | 6/2004 | Sadowski et al. |
| 7,112,187 B2 | 9/2006 | Karlsson |
| 7,357,790 B2 | 4/2008 | Hommann et al. |
| 7,442,185 B2 | 10/2008 | Amark et al. |
| 7,563,252 B2 | 7/2009 | Marshall et al. |
| 7,717,877 B2 | 5/2010 | Lavi et al. |

(Continued)

FOREIGN PATENT DOCUMENTS

| | | |
|---|---|---|
| DE | 102004060146 A1 | 8/2005 |
| EP | 2083887 B1 | 8/2009 |

(Continued)

*Primary Examiner* — Emily L Schmidt

(74) *Attorney, Agent, or Firm* — The Webb Law Firm

(57)　　ABSTRACT

Provided herein is a subassembly for a drug delivery device, including a housing, a displaceable needle cover having a distal end having a flange, the needle cover being received within the housing and configured to have a pre-use position in which the needle cover extends from the housing and a use position in which the needle cover is at least partially displaced into the housing. Displacement of the needle cover into the housing actuates the drug delivery device. The subassembly further includes a cap assembly, comprising configured to prevent movement of the needle cover to the use position.

4 Claims, 21 Drawing Sheets

(56) References Cited

U.S. PATENT DOCUMENTS

| | | | |
|---|---|---|---|
| 7,879,007 B2 | 2/2011 | Hommann | |
| 7,988,675 B2 | 8/2011 | Gillespie, III et al. | |
| 8,021,335 B2 | 9/2011 | Lesch, Jr. | |
| 8,038,649 B2 | 10/2011 | Kronestedt | |
| 8,062,255 B2 | 11/2011 | Brunnberg et al. | |
| 8,172,797 B2 | 5/2012 | Hogdahl | |
| 8,177,745 B2 | 5/2012 | Brechbuehler et al. | |
| 8,317,751 B2 | 11/2012 | Habeshaw et al. | |
| 8,337,472 B2 | 12/2012 | Edginton et al. | |
| 8,376,998 B2 | 2/2013 | Daily et al. | |
| 8,409,149 B2 | 4/2013 | Hommann et al. | |
| 8,496,619 B2 | 7/2013 | Kramer et al. | |
| 8,679,061 B2 | 3/2014 | Julian et al. | |
| 8,715,246 B2 | 5/2014 | Giambattista et al. | |
| 8,747,357 B2 | 6/2014 | Stamp et al. | |
| 8,758,301 B2 | 6/2014 | Shang et al. | |
| 8,932,254 B2 | 1/2015 | Eaton | |
| 8,945,049 B2 | 2/2015 | Hommann et al. | |
| 8,956,331 B2 | 2/2015 | Johansen et al. | |
| 8,968,236 B2 | 3/2015 | Jennings et al. | |
| 8,992,477 B2 | 3/2015 | Raday et al. | |
| 8,998,855 B2 | 4/2015 | Hudson et al. | |
| 9,011,375 B2 | 4/2015 | Holmqvist et al. | |
| 9,033,932 B2 | 5/2015 | Holmqvist | |
| 9,072,833 B2 | 7/2015 | Jennings et al. | |
| 9,078,978 B2 | 7/2015 | Schraga | |
| 9,084,849 B2 | 7/2015 | Edwards et al. | |
| 9,125,988 B2 | 9/2015 | Karlsson | |
| 9,180,256 B2 | 11/2015 | Eaton | |
| 9,180,259 B2 | 11/2015 | Lesch, Jr. | |
| 9,186,462 B2 | 11/2015 | Lanzi et al. | |
| 9,199,038 B2 | 12/2015 | Daniel | |
| 9,199,041 B2 | 12/2015 | Edginton | |
| 9,205,199 B2 | 12/2015 | Kemp et al. | |
| 9,216,251 B2 | 12/2015 | Daniel | |
| 9,259,536 B2 | 2/2016 | Gillespie, III et al. | |
| 9,302,047 B2 | 4/2016 | Alexandersson | |
| 9,327,084 B2 | 5/2016 | Evans | |
| 9,352,099 B2 | 5/2016 | Roberts et al. | |
| 9,358,345 B2 | 6/2016 | Brereton et al. | |
| 9,364,610 B2 | 6/2016 | KraMer et al. | |
| 9,364,611 B2 | 6/2016 | KraMer et al. | |
| 9,427,528 B2 | 8/2016 | Hommann et al. | |
| 9,427,531 B2 | 8/2016 | Hourmand et al. | |
| 9,446,195 B2 | 9/2016 | Kramer et al. | |
| 9,486,583 B2 | 11/2016 | Lannan et al. | |
| 9,522,233 B2 | 12/2016 | Bicknell et al. | |
| 9,526,837 B2 | 12/2016 | Carrel et al. | |
| 9,533,099 B2 | 1/2017 | Maritan | |
| 9,533,102 B2 | 1/2017 | Lesch, Jr. | |
| 9,586,011 B2 | 3/2017 | Roberts et al. | |
| 9,604,011 B2 | 3/2017 | Roberts et al. | |
| 9,616,181 B2 | 4/2017 | Kemp et al. | |
| 9,629,959 B2 | 4/2017 | Lesch | |
| 9,724,480 B2 | 8/2017 | Harms et al. | |
| 9,744,306 B2 | 8/2017 | Cowe | |
| 9,764,092 B2 | 9/2017 | Cabiri | |
| 9,764,101 B2 | 9/2017 | McLoughlin et al. | |
| 9,789,257 B2 | 10/2017 | Travanty | |
| 9,855,392 B2 | 1/2018 | Hommann et al. | |
| 9,867,942 B2 | 1/2018 | Alexandersson | |
| 9,867,949 B2 | 1/2018 | Sund et al. | |
| 9,872,961 B2 | 1/2018 | Fourt et al. | |
| 9,901,674 B2 | 2/2018 | McLoughlin et al. | |
| 9,913,943 B2 | 3/2018 | Fourt et al. | |
| 9,925,342 B2 | 3/2018 | Carrel et al. | |
| 9,950,125 B2 | 4/2018 | Wotton et al. | |
| 9,956,353 B2 | 5/2018 | Rao et al. | |
| 9,981,084 B2 | 5/2018 | Kadamus et al. | |
| 9,999,734 B2 | 6/2018 | Cowe | |
| 10,046,115 B2 | 8/2018 | Bokelman et al. | |
| 10,080,847 B2 | 9/2018 | Roberts et al. | |
| 10,086,145 B2 | 10/2018 | Cabiri et al. | |
| 10,086,152 B2 | 10/2018 | Imai et al. | |
| 10,092,073 B2 | 10/2018 | Wagoner | |
| 10,092,698 B2 | 10/2018 | Park et al. | |
| 10,092,703 B2 | 10/2018 | Mounce et al. | |
| 10,105,496 B2 | 10/2018 | Aneas | |
| 10,118,001 B2 | 11/2018 | Fourt et al. | |
| 10,130,774 B2 | 11/2018 | Daniel | |
| 10,137,255 B2 | 11/2018 | Kemp | |
| 10,137,256 B2 | 11/2018 | Taal et al. | |
| 10,149,939 B2 | 12/2018 | Giambattista et al. | |
| 10,159,791 B2 | 12/2018 | Guillermo | |
| 10,159,800 B2 | 12/2018 | Sall | |
| 10,183,121 B2 | 1/2019 | Cowe | |
| 10,252,005 B2 | 4/2019 | Row et al. | |
| 10,272,210 B2 | 4/2019 | Keitel | |
| 10,300,218 B2 | 5/2019 | Stefanov et al. | |
| 10,307,545 B2 | 6/2019 | Maxfield | |
| 10,335,553 B2 | 7/2019 | Bendek | |
| 10,350,356 B2 | 7/2019 | Hirschel et al. | |
| 10,363,377 B2 | 7/2019 | Atterbury et al. | |
| 10,363,378 B2 | 7/2019 | Moore | |
| 10,376,641 B2 | 8/2019 | Hirschel et al. | |
| 10,384,009 B2 | 8/2019 | Olson et al. | |
| 10,406,294 B2 | 9/2019 | Ward et al. | |
| 10,417,937 B2 | 9/2019 | Galliot et al. | |
| 10,485,934 B2 | 11/2019 | Bostrom | |
| 10,493,212 B2 | 12/2019 | Tschirren et al. | |
| 10,493,213 B2 | 12/2019 | Hommann et al. | |
| 10,500,337 B2 | 12/2019 | Fabien et al. | |
| 10,525,201 B2 | 1/2020 | Brunnberg et al. | |
| 10,561,798 B2 | 2/2020 | Holland et al. | |
| 10,643,744 B2 | 5/2020 | Hopper et al. | |
| 10,646,643 B2 | 5/2020 | Cabiri et al. | |
| 10,758,683 B2 | 9/2020 | Gibson et al. | |
| 10,799,647 B2 | 10/2020 | Hostettler et al. | |
| 10,821,072 B2 | 11/2020 | Wotton et al. | |
| 10,881,799 B2 | 1/2021 | Hirschel et al. | |
| 10,888,668 B2 | 1/2021 | Mosebach et al. | |
| 10,894,127 B2 | 1/2021 | Tschirren et al. | |
| 10,912,890 B2 | 2/2021 | Gaillot et al. | |
| 10,967,128 B2 | 4/2021 | Holmqvist | |
| 10,973,984 B2 | 4/2021 | Fournier et al. | |
| 11,040,145 B1 | 6/2021 | Chu | |
| 11,097,065 B2 | 8/2021 | Newton et al. | |
| 11,103,647 B2 * | 8/2021 | Bernhard | A61M 5/3213 |
| 11,147,932 B2 | 10/2021 | Alexandersson | |
| 2003/0105430 A1 | 6/2003 | Lavi et al. | |
| 2005/0222539 A1 | 10/2005 | Gonzales et al. | |
| 2011/0196339 A1 | 8/2011 | Hirschel et al. | |
| 2013/0303985 A1 | 11/2013 | Wotton et al. | |
| 2013/0331796 A1 | 12/2013 | Wozencroft | |
| 2014/0128808 A1 | 5/2014 | Keitel | |
| 2015/0088077 A1 | 3/2015 | Kemp et al. | |
| 2015/0202379 A1 | 7/2015 | Raday et al. | |
| 2015/0273162 A1 | 10/2015 | Holmqvist | |
| 2016/0030675 A1 | 2/2016 | Draper et al. | |
| 2016/0074584 A1 | 3/2016 | Carmel et al. | |
| 2016/0074585 A1 | 3/2016 | Hommann et al. | |
| 2016/0129195 A1 | 5/2016 | Jennings et al. | |
| 2016/0129200 A1 | 5/2016 | Jennings et al. | |
| 2016/0151586 A1 | 6/2016 | Kemp | |
| 2016/0175523 A1 | 6/2016 | Blomberg | |
| 2016/0199588 A1 | 7/2016 | Kemp | |
| 2016/0199589 A1 | 7/2016 | Plumptre | |
| 2016/0220761 A1 | 8/2016 | Shetty et al. | |
| 2016/0303323 A1 | 10/2016 | Saussaye et al. | |
| 2016/0303327 A1 | 10/2016 | Moren | |
| 2016/0317750 A1 | 11/2016 | Jugl et al. | |
| 2016/0317753 A1 | 11/2016 | Jugl et al. | |
| 2016/0325044 A1 | 11/2016 | Tschirren et al. | |
| 2017/0007764 A1 | 1/2017 | Saussaye | |
| 2017/0021103 A1 | 1/2017 | Mosebach et al. | |
| 2017/0043103 A1 | 2/2017 | Wotton et al. | |
| 2017/0072142 A1 | 3/2017 | Perthu | |
| 2017/0080163 A1 | 3/2017 | Bendek et al. | |
| 2017/0136192 A1 | 5/2017 | Stefansen et al. | |
| 2017/0173270 A1 | 6/2017 | Nakamura et al. | |
| 2017/0182242 A1 | 6/2017 | Galitz et al. | |
| 2017/0203041 A1 | 7/2017 | Julian et al. | |
| 2017/0224921 A1 | 8/2017 | Takabatake et al. | |
| 2017/0252518 A1 | 9/2017 | Holmqvist | |

(56) References Cited

U.S. PATENT DOCUMENTS

| | | |
|---|---|---|
| 2017/0258998 A1 | 9/2017 | Stamp |
| 2017/0290990 A1 | 10/2017 | Wu |
| 2017/0340824 A1 | 11/2017 | Maritan |
| 2017/0361015 A1 | 12/2017 | McCullough |
| 2017/0361021 A1 | 12/2017 | Wotton et al. |
| 2018/0028753 A1 | 2/2018 | Wilmot et al. |
| 2018/0036491 A1 | 2/2018 | Maxfield |
| 2018/0036492 A1 | 2/2018 | Schader et al. |
| 2018/0043108 A1 | 2/2018 | Mesa et al. |
| 2018/0078713 A1 | 3/2018 | Hommann et al. |
| 2018/0079119 A1 | 3/2018 | Morris et al. |
| 2018/0093046 A1 | 4/2018 | Hourmand et al. |
| 2018/0099099 A1 | 4/2018 | Sund et al. |
| 2018/0104413 A1* | 4/2018 | Mcloughlin .......... A61M 5/204 |
| 2018/0110926 A1 | 4/2018 | Schrul et al. |
| 2018/0110936 A1 | 4/2018 | Hatch et al. |
| 2018/0126083 A1 | 5/2018 | Schmid et al. |
| 2018/0133407 A1 | 5/2018 | Kemp et al. |
| 2018/0140781 A1 | 5/2018 | Kemp et al. |
| 2018/0140782 A1 | 5/2018 | Kemp et al. |
| 2018/0147358 A1 | 5/2018 | Julian et al. |
| 2018/0154078 A1 | 6/2018 | Mosebach et al. |
| 2018/0154085 A1 | 6/2018 | Mosebach et al. |
| 2018/0154089 A1 | 6/2018 | Mosebach et al. |
| 2018/0161504 A1 | 6/2018 | Kemp et al. |
| 2018/0169342 A1 | 6/2018 | Mosebach et al. |
| 2018/0169349 A1 | 6/2018 | Mosebach et al. |
| 2018/0177952 A1 | 6/2018 | Bengtsson et al. |
| 2018/0200445 A1 | 7/2018 | Brereton et al. |
| 2018/0207363 A1 | 7/2018 | Fabien et al. |
| 2018/0221589 A1 | 8/2018 | Vogt et al. |
| 2018/0243506 A1 | 8/2018 | Niven et al. |
| 2018/0256826 A1 | 9/2018 | Roberts et al. |
| 2018/0264196 A1 | 9/2018 | Fabien et al. |
| 2018/0289899 A1 | 10/2018 | Gould |
| 2018/0296768 A1 | 10/2018 | Gould et al. |
| 2018/0304014 A1 | 10/2018 | Knudsen et al. |
| 2018/0311438 A1 | 11/2018 | Stamp et al. |
| 2018/0326152 A1 | 11/2018 | Laiosa |
| 2018/0344946 A1 | 12/2018 | Scharf |
| 2018/0353705 A1 | 12/2018 | Andre et al. |
| 2018/0369497 A1 | 12/2018 | Schader et al. |
| 2019/0151547 A1 | 5/2019 | Cowe et al. |
| 2019/0151564 A1 | 5/2019 | Schrul et al. |
| 2019/0151565 A1 | 5/2019 | Groetzbach et al. |
| 2019/0167908 A1 | 6/2019 | Fitzgibbon et al. |
| 2019/0201634 A1 | 7/2019 | Newton et al. |
| 2019/0209786 A1 | 7/2019 | Tschirren et al. |
| 2019/0240394 A1 | 8/2019 | Horvath et al. |
| 2019/0269856 A1 | 9/2019 | Baumeyer et al. |
| 2020/0009323 A1 | 1/2020 | Nair et al. |
| 2020/0030539 A1 | 1/2020 | Shabudin, Jr. |
| 2020/0030547 A1 | 1/2020 | Wang et al. |
| 2020/0035047 A1 | 1/2020 | Arnold |
| 2020/0046910 A1 | 2/2020 | Maxfield et al. |
| 2020/0061309 A1 | 2/2020 | Alexandersson |
| 2020/0139046 A1 | 5/2020 | Jacobsen |
| 2020/0147311 A1 | 5/2020 | Dugand et al. |
| 2020/0164138 A1 | 5/2020 | Holmqvist |
| 2020/0254181 A1 | 8/2020 | Mosebach et al. |
| 2020/0289740 A1 | 9/2020 | Tamtoro et al. |
| 2020/0330699 A1 | 10/2020 | Burren et al. |
| 2021/0015741 A1 | 1/2021 | Wotton et al. |
| 2021/0085884 A1 | 3/2021 | Liniger et al. |
| 2021/0093790 A1 | 4/2021 | Mosebach et al. |
| 2021/0106756 A1 | 4/2021 | Alexandersson |
| 2021/0268201 A1 | 9/2021 | Bostrom |
| 2021/0275750 A1 | 9/2021 | Helmer et al. |
| 2022/0016356 A1* | 1/2022 | Alexandersson ... A61M 5/3204 |
| 2022/0016359 A1 | 1/2022 | Alexandersson |

FOREIGN PATENT DOCUMENTS

| | | |
|---|---|---|
| EP | 2323717 B1 | 5/2011 |
| EP | 2525845 B1 | 11/2012 |
| EP | 2588168 B1 | 5/2013 |
| EP | 2654854 B1 | 10/2013 |
| EP | 2931338 B1 | 10/2015 |
| EP | 2953667 B1 | 12/2015 |
| EP | 3107605 B1 | 12/2016 |
| EP | 1850892 A1 | 11/2017 |
| EP | 3320932 A1 | 5/2018 |
| EP | 3407939 B1 | 12/2018 |
| EP | 3474928 B1 | 5/2019 |
| EP | 3490647 B1 | 6/2019 |
| EP | 3515538 B1 | 7/2019 |
| EP | 3519020 B1 | 8/2019 |
| EP | 3525849 | 8/2019 |
| EP | 3541453 A1 | 9/2019 |
| JP | 2015516845 A | 6/2015 |
| WO | 2003041768 A1 | 5/2003 |
| WO | 2003047663 A1 | 6/2003 |
| WO | 2004098687 A1 | 11/2004 |
| WO | 2005097238 A3 | 10/2005 |
| WO | 2008059233 A1 | 5/2008 |
| WO | 2009019436 A1 | 7/2008 |
| WO | 2009019437 A1 | 2/2009 |
| WO | 2009019438 A1 | 2/2009 |
| WO | 2009019439 A1 | 2/2009 |
| WO | 2009019440 A1 | 2/2009 |
| WO | 2013006119 A1 | 1/2013 |
| WO | 2013152323 A1 | 10/2013 |
| WO | 2017187177 A1 | 11/2017 |
| WO | 2017223354 A1 | 12/2017 |
| WO | 2018004842 A1 | 1/2018 |
| WO | 2018010947 A1 | 1/2018 |
| WO | 2018018164 A1 | 2/2018 |
| WO | 2018018165 A1 | 2/2018 |
| WO | 2018037034 A1 | 3/2018 |
| WO | 2018069031 A1 | 4/2018 |
| WO | 2018082886 A1 | 5/2018 |
| WO | 2018091262 A1 | 5/2018 |
| WO | 2018167640 A1 | 9/2018 |
| WO | 2018172223 A1 | 9/2018 |
| WO | 2018178127 A1 | 10/2018 |
| WO | 2018192750 A1 | 10/2018 |
| WO | 2018197774 A1 | 11/2018 |
| WO | 2018206583 A1 | 11/2018 |
| WO | 2018215271 A1 | 11/2018 |
| WO | 2018226565 A1 | 12/2018 |
| WO | 2020015986 A1 | 1/2020 |

* cited by examiner

335

340

340

1

RIGID NEEDLE SHIELD REMOVER WITH DROP TEST FEATURE FOR AUTOINJECTOR

CROSS-REFERENCE TO RELATED APPLICATIONS

This application is the United States national phase of International Application No. PCT/EP2020/055011 filed Feb. 26, 2020, and claims priority to Europe patent application No. 19305229.7 filed Feb. 26, 2019, the entire disclosures of which are hereby incorporated by reference in their entirety.

BACKGROUND OF THE INVENTION

Field of the Invention

The present disclosure relates generally to autoinjectors and methods of assembling the same and, more specifically, to devices for removing needle shields from autoinjectors, devices for preventing unintended actuation of autoinjectors, and methods for assembling autoinjectors including such devices.

Description of Related Art

Automatic drug delivery devices, such as autoinjectors, are designed with removable shields to maintain sterility of the needle and to prevent inadvertent contact between the needle and a user. Many of these needle shields are elastomeric, and ensuring accurate placement and a firm grip between the needle shield and caps or other removal devices can be difficult, resulting in a need for excess force to remove the shield or slippage and an inability to remove the shield at all. Accordingly, a need exists in the art for a needle shield remover that can reliably be positioned for quick and easy removal of the needle shield when the autoinjector is to be used.

In addition, automatic drug delivery devices can suffer from a tendency to inadvertently actuate when a force is applied to the device. In particular, devices with "push-on" actuation can be susceptible to inadvertent actuation when the device is dropped. Accordingly, a need exists in the art for a device that can prevent unintended actuation of an autoinjector.

SUMMARY OF THE INVENTION

Provided herein is a subassembly for a drug delivery device, having a housing; a displaceable needle cover having a distal end having a flange, the needle cover received within the housing and configured to have a pre-use position in which the needle cover extends from the housing and a use position in which the needle cover is at least partially displaced into the housing, wherein displacement of the needle cover into the housing actuates the drug delivery device through interaction with a drive mechanism; and a cap assembly, including a cap remover configured to be grasped by a user and a retainer received within the cap remover and configured to engage the flange of the needle cover of the drug delivery device, wherein the arrangement of retainer relative to the flange is configured to prevent movement of the needle cover to the use position.

Also provided herein is a drug delivery device including a housing; a syringe having a needle and received at least partially within the housing; a needle cover having a flange at a distal end thereof and having a pre-use position in which the needle is positioned within the needle cover and a use position in which the needle is positioned at least partially outside of the needle cover, wherein in the use position the needle cover is configured to actuate the drug delivery device to deliver a medicament; and a cap assembly including a cap remover and a retainer received within the cap remover, the retainer configured to prevent movement of the needle cover from the pre-use position to the use position.

Further embodiments and aspects are set forth below:

A subassembly for a drug delivery device comprising: a housing; a displaceable needle cover comprising a distal end comprising a flange, the needle cover received within the housing and configured to have a pre-use position in which the needle cover extends from the housing and a use position in which the needle cover is at least partially displaced into the housing, wherein displacement of the needle cover into the housing actuates the drug delivery device through interaction with a drive mechanism; and a cap assembly, comprising: a cap remover configured to be grasped by a user; and a retainer received within the cap remover and configured to engage the flange of the needle cover of the drug delivery device, wherein the arrangement of retainer relative to the flange is configured to prevent movement of the needle cover to the use position.

The subassembly described above, wherein the retainer comprises at least one protrusion configured to engage the flange of the needle cover.

The subassembly described above, wherein the engagement of the at least one protrusion of the retainer and the flange of the needle cover prevents movement of the needle cover to the use position.

The subassembly described above, wherein the flange is arranged on an outer surface of the needle cover and the protrusion is an inward-facing protrusion arranged radially outward of the flange.

The subassembly described above, wherein the protrusion abuts the flange on a proximal end thereof.

The subassembly described above, wherein the retainer comprises at least one radially-extending protrusion and the cap remover comprises at least one opening in a sidewall thereof.

The subassembly described above, wherein the at least one radially-extending protrusion is configured to deflect radially outward when the at least one radially-extending protrusion is aligned with the at least one opening in the cap remover.

The subassembly described above, wherein the retainer is shiftable relative to the cap remover from a first position in which the at least one radially-extending protrusion is not aligned with the at least one opening in the cap remover and cannot deflect radially outward to a second position in which the at least one radially-extending protrusion is aligned with the at least one opening in the cap remover, such that the at least one radially-extending protrusion is capable of deflecting radially outward.

A drug delivery device comprising: a housing; a syringe comprising a needle and received at least partially within the housing; a needle cover comprising a flange at a distal end thereof and having a pre-use position in which the needle is positioned within the needle cover and a use position in which the needle is positioned at least partially outside of the needle cover, wherein in the use position the needle cover is configured to actuate the drug delivery device to deliver a medicament; and a cap assembly comprising a cap remover and a retainer received within the cap remover, the retainer configured to prevent movement of the needle cover from the pre-use position to the use position.

The drug delivery device described above, wherein the retainer comprises at least one protrusion configured to engage the flange of the needle cover.

The drug delivery device described above, wherein the engagement of the at least one protrusion of the retainer and the flange of the needle cover prevents movement of the needle cover to the use position.

The drug delivery device described above, wherein the retainer comprises at least one radially-extending protrusion and the cap remover comprises at least one opening in a sidewall thereof.

The drug delivery device described above, wherein the at least one radially-extending protrusion is configured to deflect radially outward when the at least one radially-extending protrusion is aligned with the at least one opening in the cap remover.

The drug delivery device described above, wherein the retainer is shiftable relative to the cap remover from a first position in which the at least one radially-extending protrusion is not aligned with the at least one opening in the cap remover and cannot deflect radially outward to a second position in which the at least one radially-extending protrusion is aligned with the at least one opening in the cap remover, such that the at least one radially-extending protrusion is capable of deflecting radially outward.

DESCRIPTION OF THE INVENTION

Figure 1A:
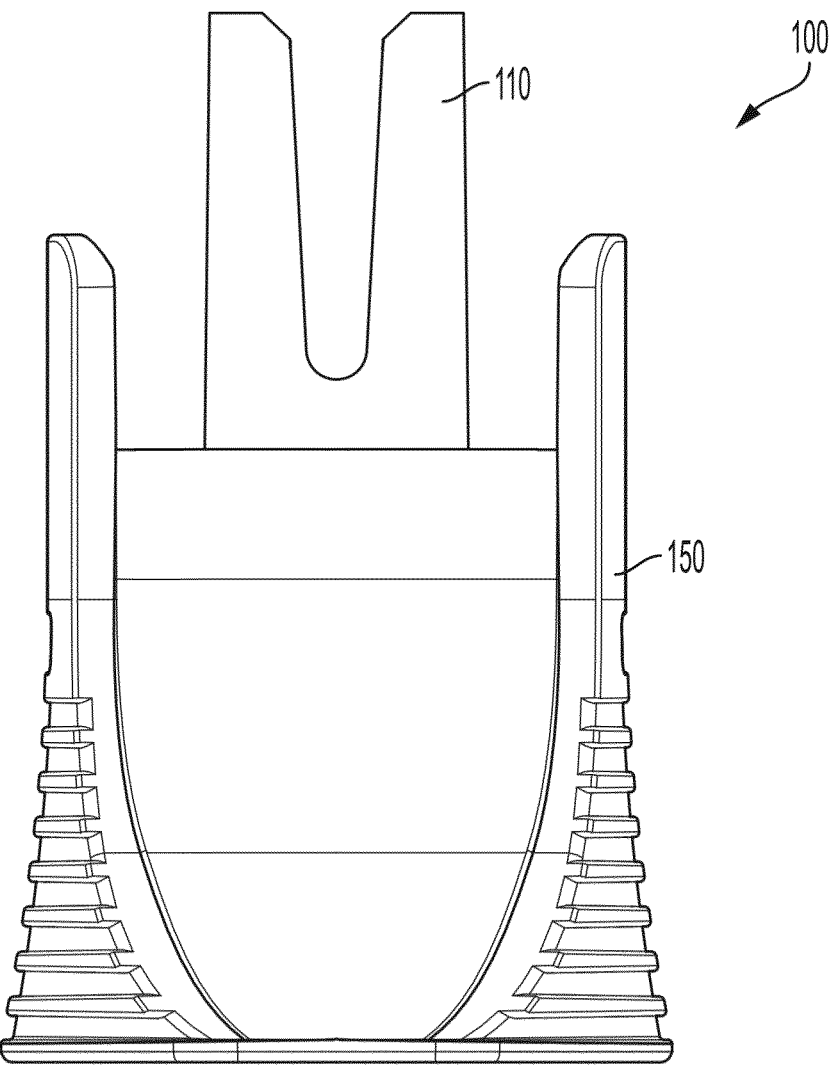
FIG. 1A is a side view of a cap assembly according to a non-limiting embodiment or aspect described herein.
Figure 1B:
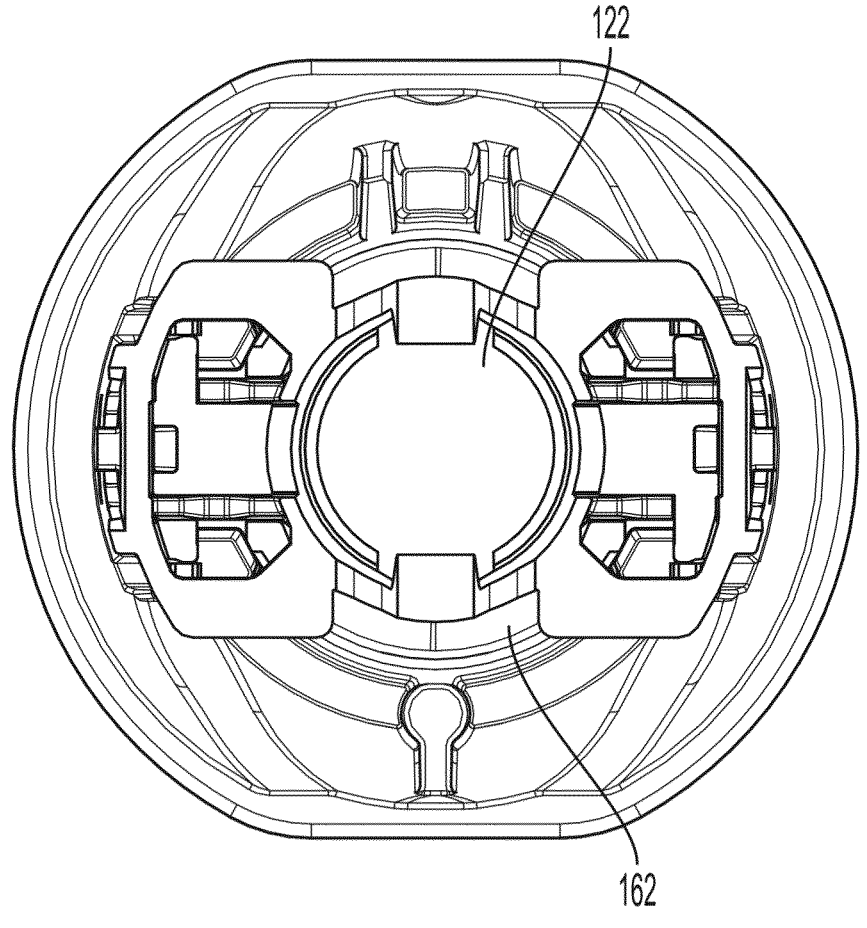
FIG. 1B is a bottom view of a cap assembly according to a non-limiting embodiment or aspect described herein.

The following description is provided to enable those skilled in the art to make and use the described embodiments contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present invention.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume various alternative variations, except where expressly specified to the contrary. It is also to be understood that the specific devices illustrated in the attached drawings, and described in the following specification, are simply exemplary embodiments of the invention. Hence, specific dimensions and other physical characteristics related to the embodiments disclosed herein are not to be considered as limiting.

Provided herein is a cap assembly for a drug delivery device including a needle. In non-limiting embodiments or aspects, the drug delivery device is an autoinjector or other similar device for automatic or manual delivery of a substance to a user. With reference to FIGS. 1-6, shown is a cap assembly (100), which in non-limiting embodiments or aspects is a shield removal assembly including a retainer (110) and a cap remover (150). Retainer (110) is nested within cap remover (150). In non-limiting embodiments or aspects, cap remover (150) is flared at a distal end thereof to form an ergonomic gripping surface to allow a user to firmly grip the cap remover. Retainer (110) and cap remover (150) can be formed of any rigid material, for example, and without limitation, plastics and the like.

FIGS. 2A, 2B, and 5A-5C show exploded views of a non-limiting embodiment or aspect of the cap assembly described herein. Cap remover (150) includes proximal end (155), which is configured to be closest to the housing, and a distal end (160). In non-limiting embodiments or aspects, proximal end (155) of cap remover (150) includes two or more arms that engage with a housing (not shown) of an autoinjector. In such non-limiting embodiments or aspects, the arms of the cap remover (150) include at least one projection or shoulder to allow secure, releasable engagement with the housing of the autoinjector. The distal end (160) of cap remover (150) includes at least one opening (162) therethrough. In non-limiting embodiments or aspects, cap remover (150) includes in a sidewall thereof at least one opening (170). In non-limiting embodiments or aspects, cap remover (150) includes two openings (170). In non-limiting embodiments or aspects, cap remover (150) includes two openings (170) that are located on opposite sides of the cap remover (150).

With continued reference to FIGS. 1, 2A, 2B, 4, 5A, and 5B, retainer (110) includes proximal (115, closest to the housing) and distal (120) ends. In non-limiting embodiments or aspects, proximal end (115) of retainer (110) includes two or more arms that engage with the needle shield (not shown) of an autoinjector. In such non-limiting embodiments or aspects, the arms of the retainer (110) include at least one projection to allow secure engagement with the needle shield. The distal end (120) of retainer (110) includes at least one opening (122) therethrough. In non-limiting embodiments, the distal end (120) of the retainer (110) is configured to abut the distal end (160) of the cap remover (150). In non-limiting embodiments or aspects, the opening (162) in the distal end (160) of the cap remover (150) is of a larger diameter than the opening (122) in the distal end (120) of the retainer (110). In non-limiting embodiments or aspects, this difference in diameter allows the retainer (110) to be introduced into the cap remover (150) through the opening (162) in the distal end (160) of the cap remover (150).

Figure 3:
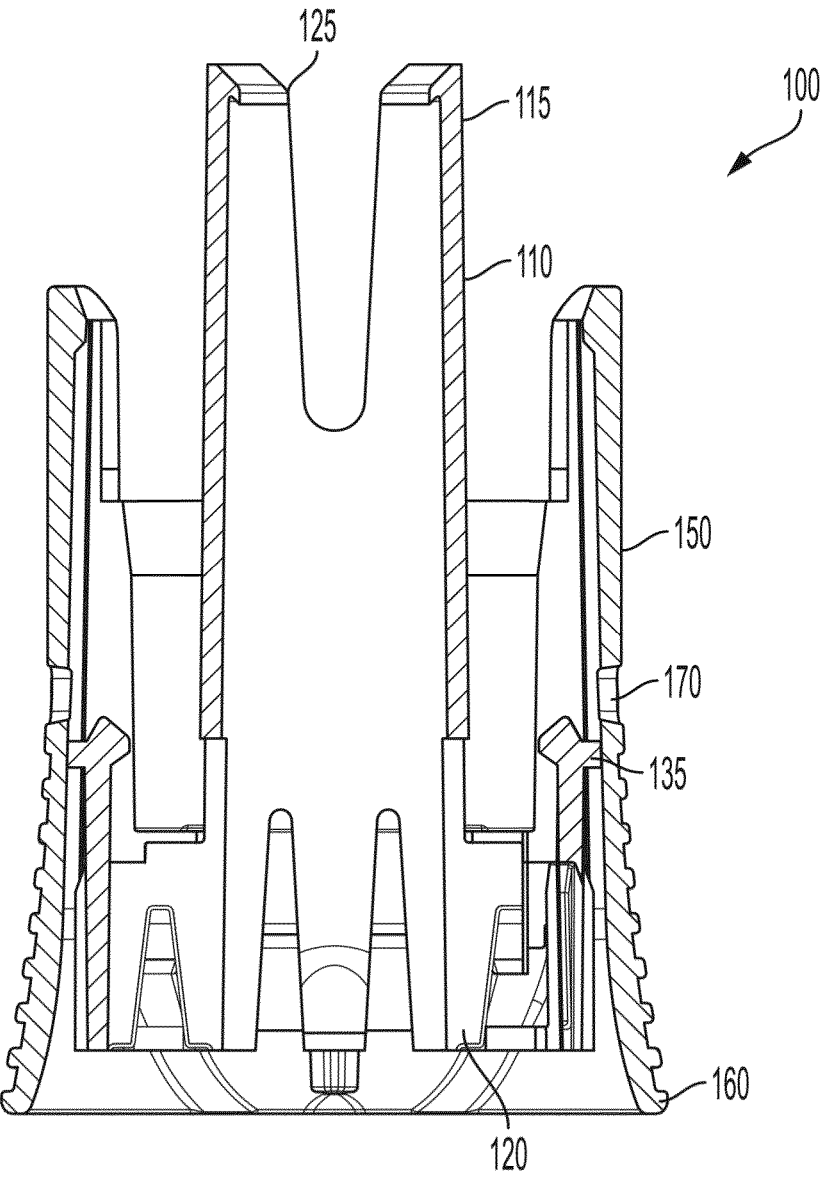
FIG. 3 is a cross-sectional view of a cap assembly according to a non-limiting embodiment or aspect described herein.
Figure 4A:
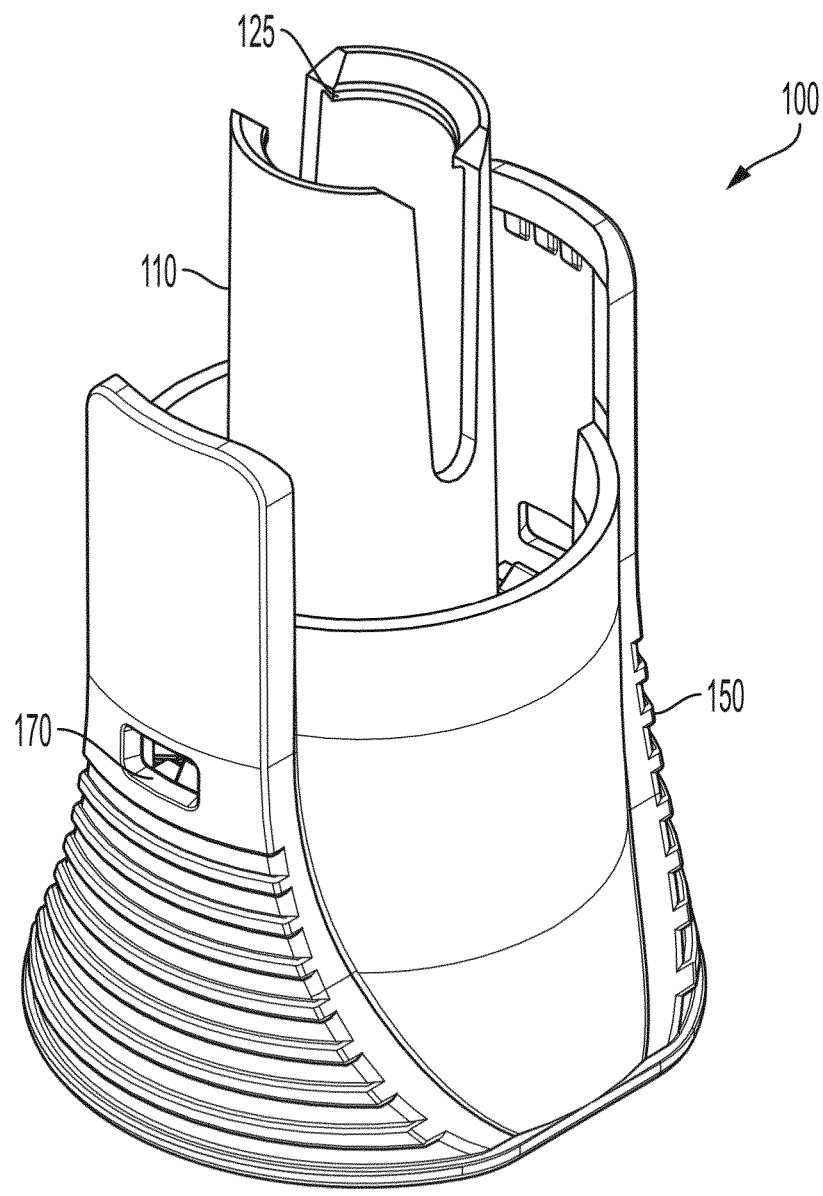
FIG. 4A is a perspective view of a cap assembly according to a non-limiting embodiment or aspect described herein.
Figure 4B:
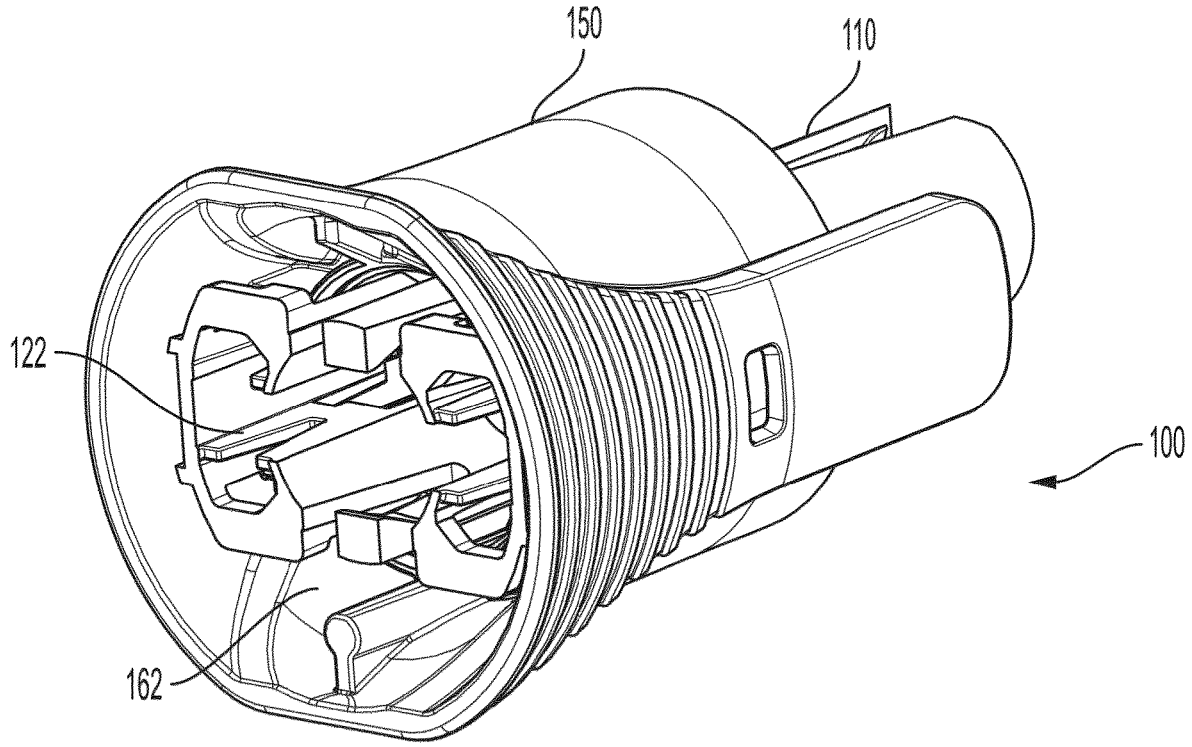
FIG. 4B is a perspective view of a cap assembly according to a non-limiting embodiment or aspect described herein.
Figure 5A:
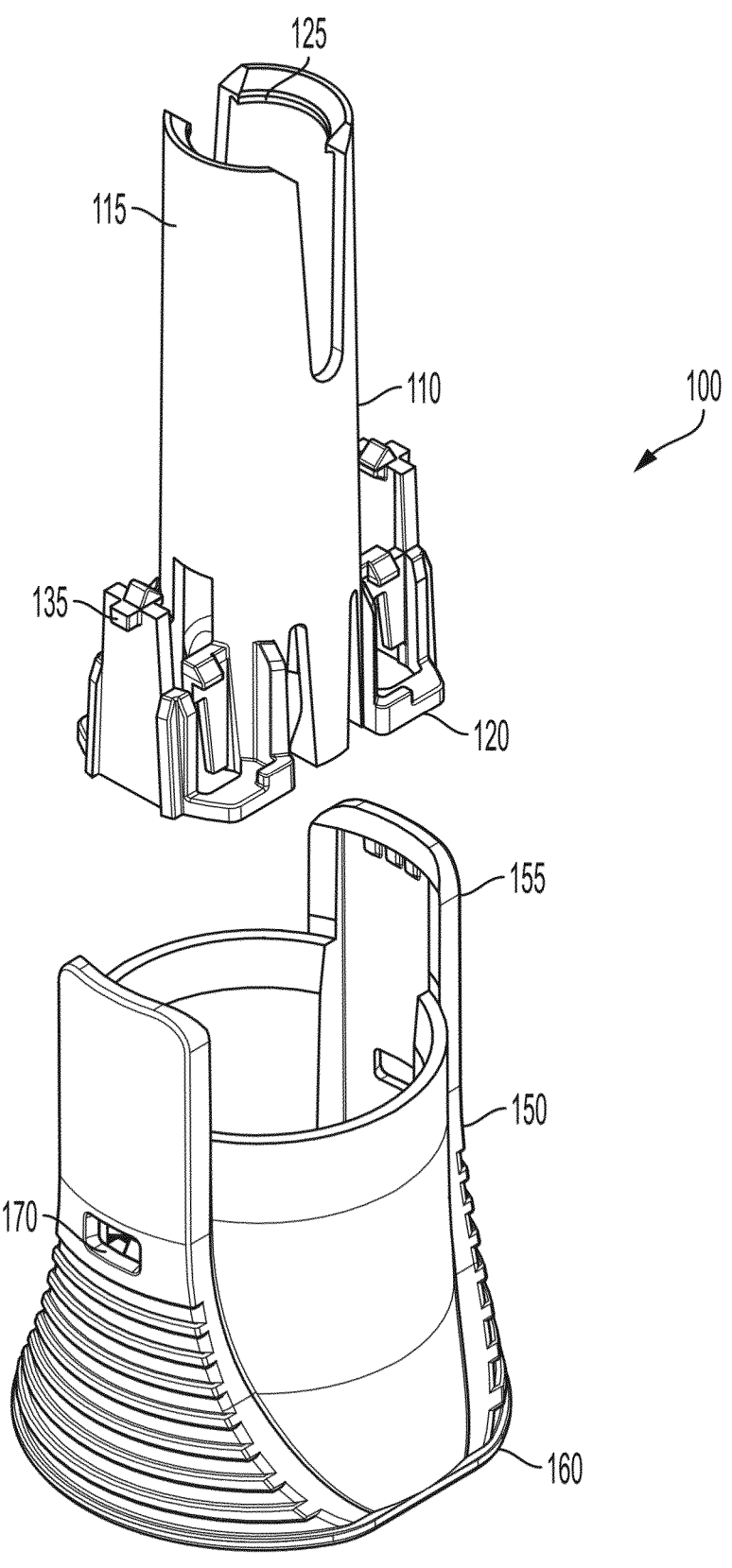
FIG. 5A is an exploded perspective view of a cap assembly according to a non-limiting embodiment or aspect described herein.
Figure 5B:
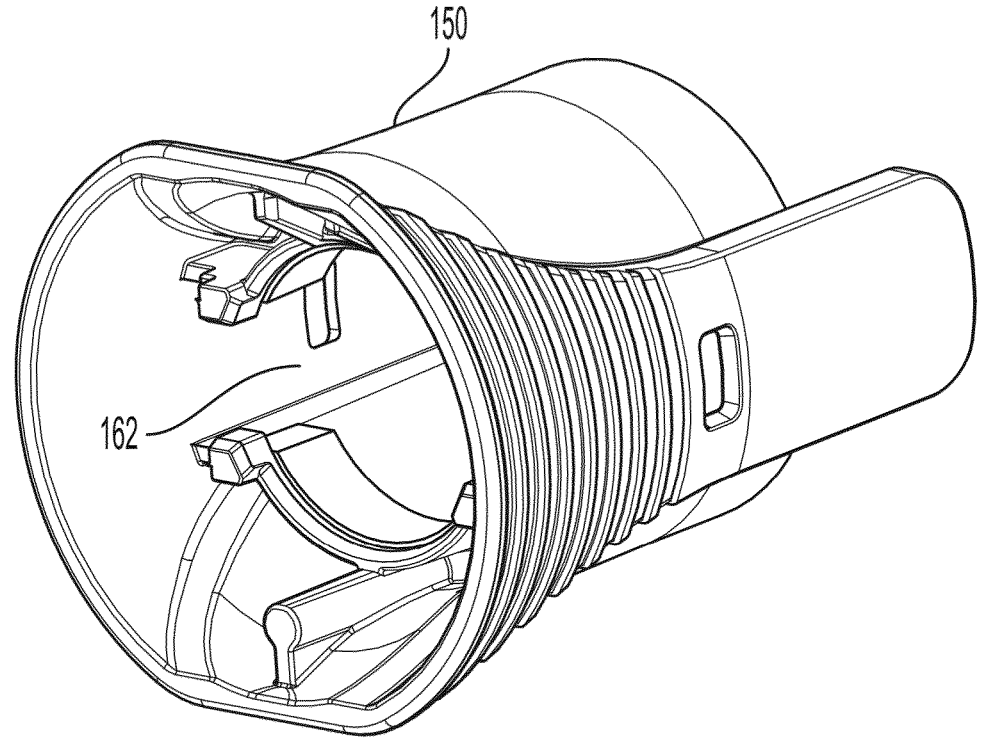
FIG. 5B is a perspective view of a cap remover of a cap assembly according to a non-limiting embodiment or aspect described herein.
Figure 5C:
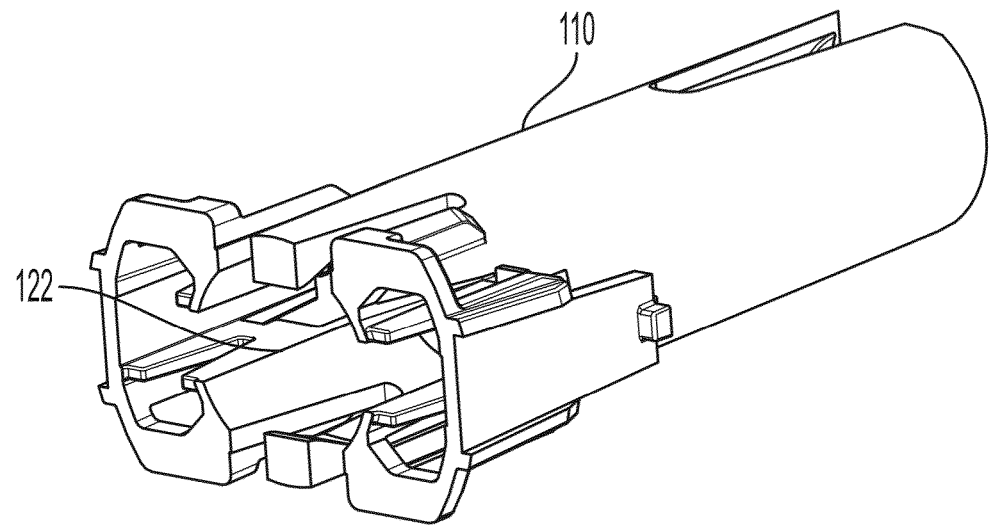
FIG. 5C is a perspective view of a retainer of a cap assembly according to a non-limiting embodiment or aspect described herein.
Figure 6:
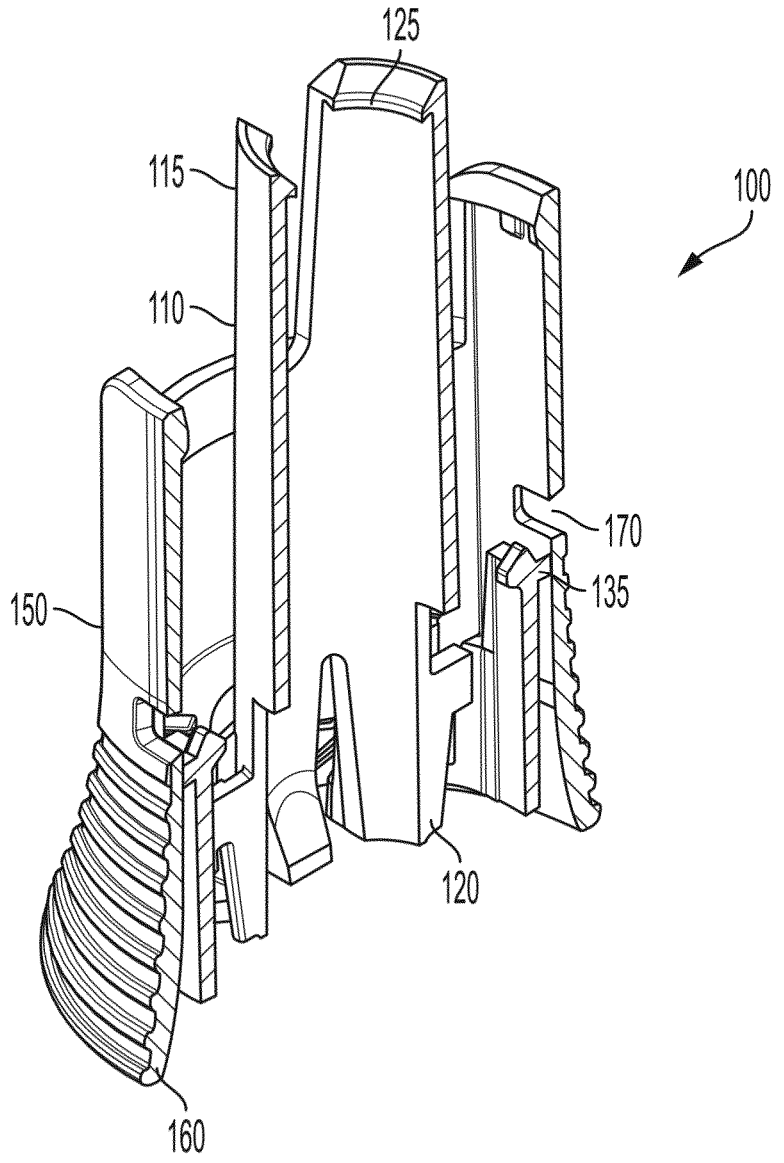
FIG. 6 is a cross-sectional perspective view of a cap assembly according to a non-limiting embodiment or aspect described herein.

As described previously, proximal end (115) of retainer (110) can include at least one grasping feature, such as a projection, to allow secure engagement with a needle shield. Turning to FIGS. 3 and 6, shown is a cap assembly according to a non-limiting embodiment or aspect, where the retainer (110) includes at least one grasping feature (125) at a proximal end (115) thereof. The at least one grasping feature can be at least one protrusion (125), and can be configured such that it is capable of gripping a needle shield by a flange thereof.

In non-limiting embodiments or aspects, the retainer (110) and cap remover (150) of the cap assembly (100) are configured or arranged such that the needle shield and/or syringe of an autoinjector (not shown) can be shifted relative to the retainer by introducing a device, such as a tool, through the openings (122, 162) in the distal ends (120, 160) of the retainer (110) and cap remover (150), respectively. Placing a tool through the openings in the cap remover and retainer allows the needle shield and syringe to be displaced proximally, and thus allows for adjustment of the positioning of the projections (125) relative to the needle shield to ensure a secure grip between the retainer (110) and the needle shield.

With continued reference to FIGS. 3 and 6, as described above in non-limiting embodiments or aspects the cap remover (150) includes at least one opening (170) in a sidewall thereof. The at least one opening (170) is configured to allow at least one radially-extending protrusion (135) on retainer (110) to extend therethrough. In the non-limiting embodiment or aspect shown in FIGS. 3 and 6, at least one radially-extending protrusion (135) extends from an arm that extends proximally from the distal end (120) of the retainer (110). In other non-limiting embodiments or aspects (not shown), the at least one radially-extending protrusion (135) is positioned on a main body of the retainer (110).

Figure 2A:
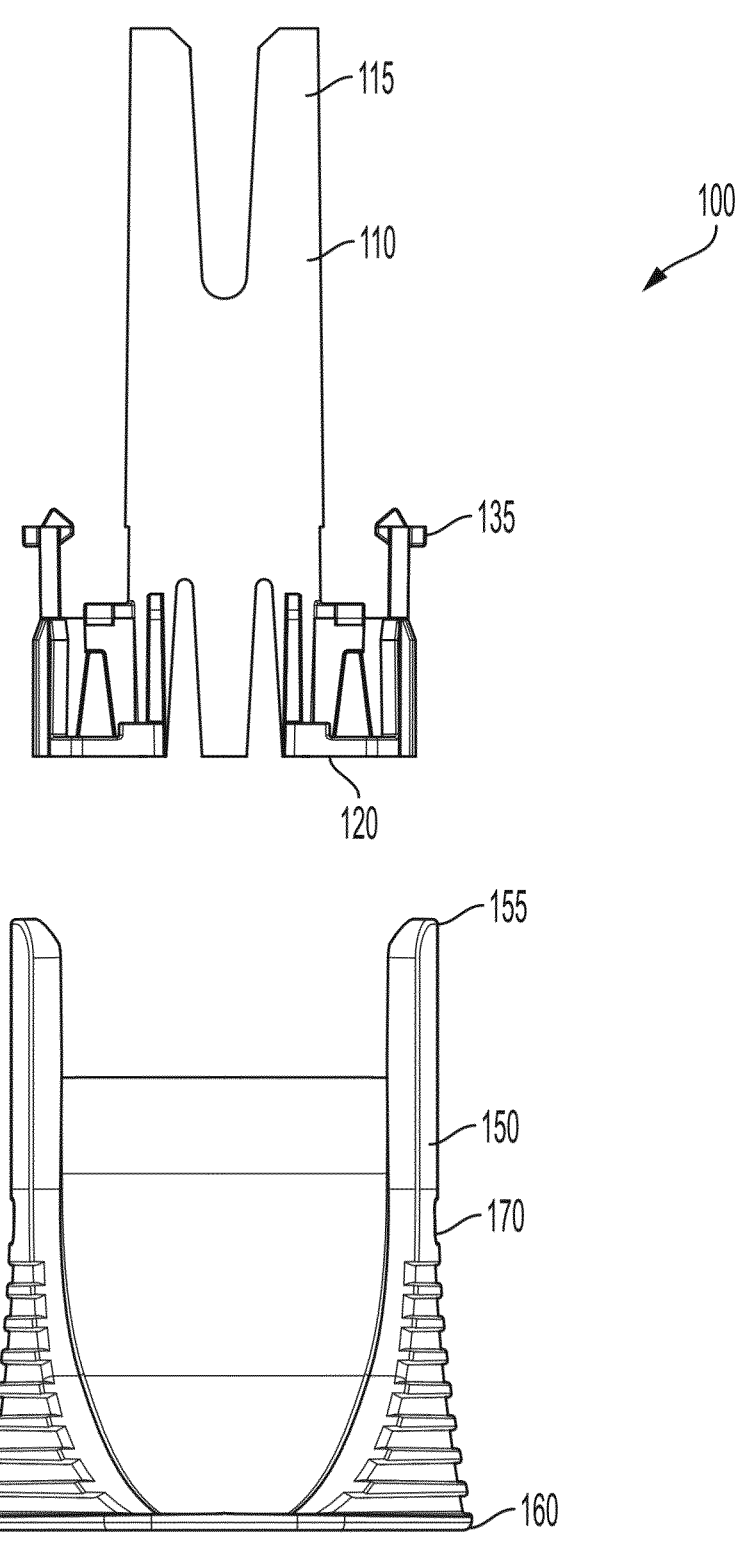
FIG. 2A is an exploded view of a cap assembly according to a non-limiting embodiment or aspect described herein.
Figure 2B:
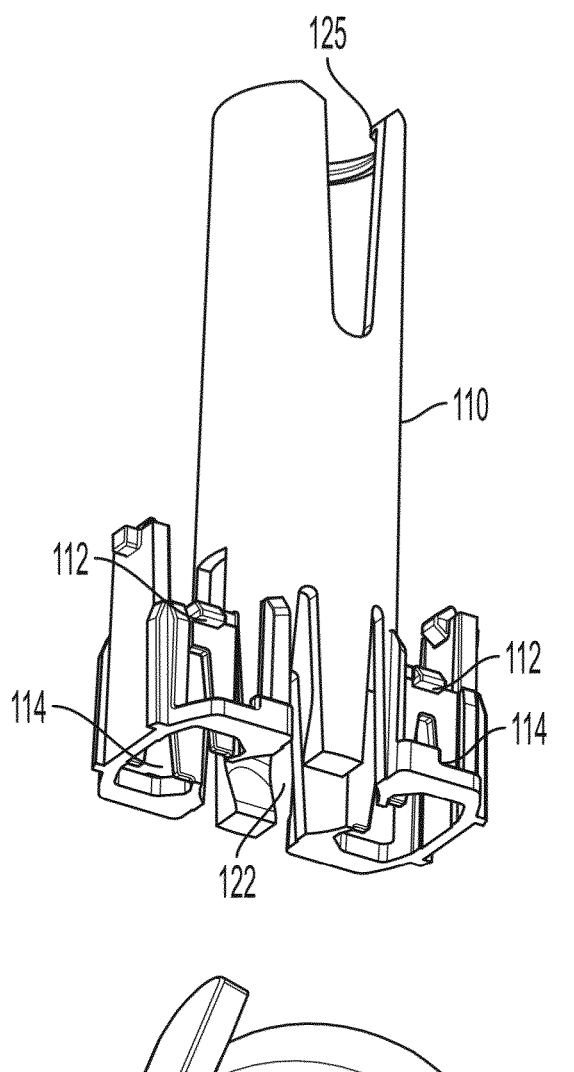
FIG. 2B is a perspective view of the cap assembly as shown in FIG. 2A.
Figure 2B:
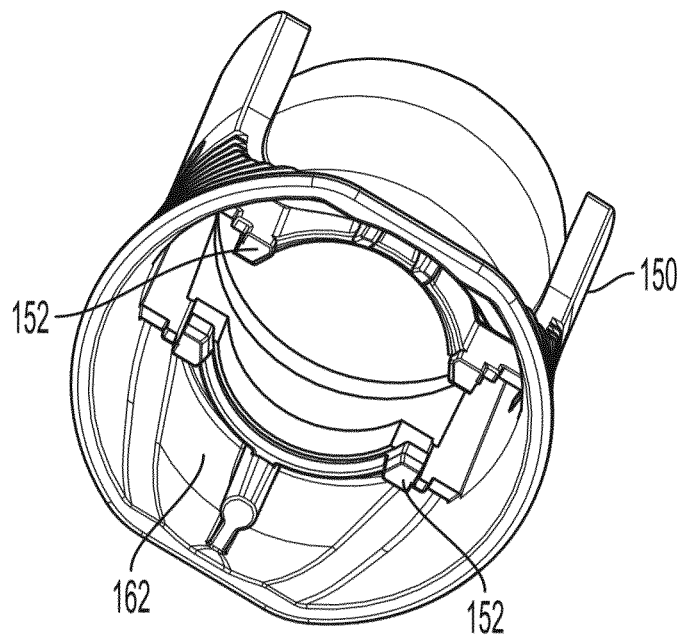

With reference to FIGS. 2A and 2B, a lag arrangement is provided between the cap remover (150) and the retainer (110) during removal of the cap assembly (100). Retainer (110) is received within cap remover (150) such that at least one protrusion (112) is arranged proximally of at least one shoulder (152) of cap remover (150). In non-limiting embodiments or aspects, the at least one protrusion (112) prevents the retainer (110) from being displaced distally out of the cap remover (150), by virtue of engagement with a proximal surface of the at least one shoulder (152). In non-limiting embodiments or aspects, the retainer (110) further includes at least one flange (114), arranged distally of the at least one shoulder (152) of the cap remover (150). In this way, the retainer (110) is prevented from being displaced proximally out of the cap remover (150) by virtue of engagement of a proximal surface of the at least one flange (114) with a distal surface of the at least one shoulder (152). The longitudinal space between the at least one protrusion (112) and the at least one flange (114) on the retainer (110) results in a predetermined amount of "play" between these components. Accordingly, in non-limiting embodiments or aspects, when the cap remover (150) is pulled distally to remove the cap assembly (100) from a drug delivery device to which it is attached, cap remover (150) is pulled a certain distance before the at least one shoulder (152) engages the at least one protrusion (112) of the retainer (110). This results in a lag between the initiation of movement of the cap remover (150) and initiation of movement of the retainer (110). When cap remover (150) moves sufficiently such that the at least one shoulder (152) engages with the at least one protrusion (112), the retainer (110) begins to be pulled away from the drug delivery device, and, because of the positioning of the at least one projection (125) relative to the needle shield, the needle shield begins to be pulled away from the syringe and needle.

Figure 7:
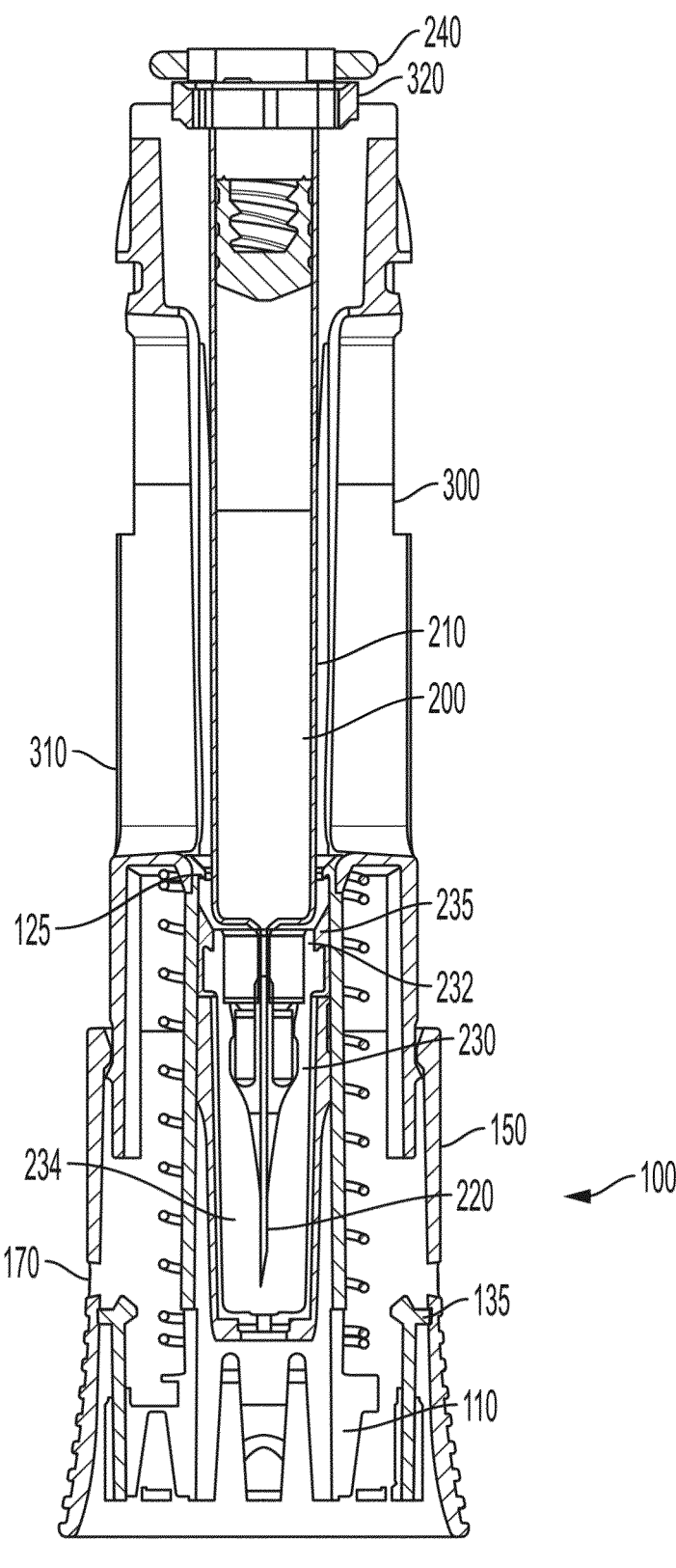
FIG. 7 is a cross-sectional view of an autoinjector including a cap assembly according to a non-limiting embodiment or aspect described herein.
Figure 8:
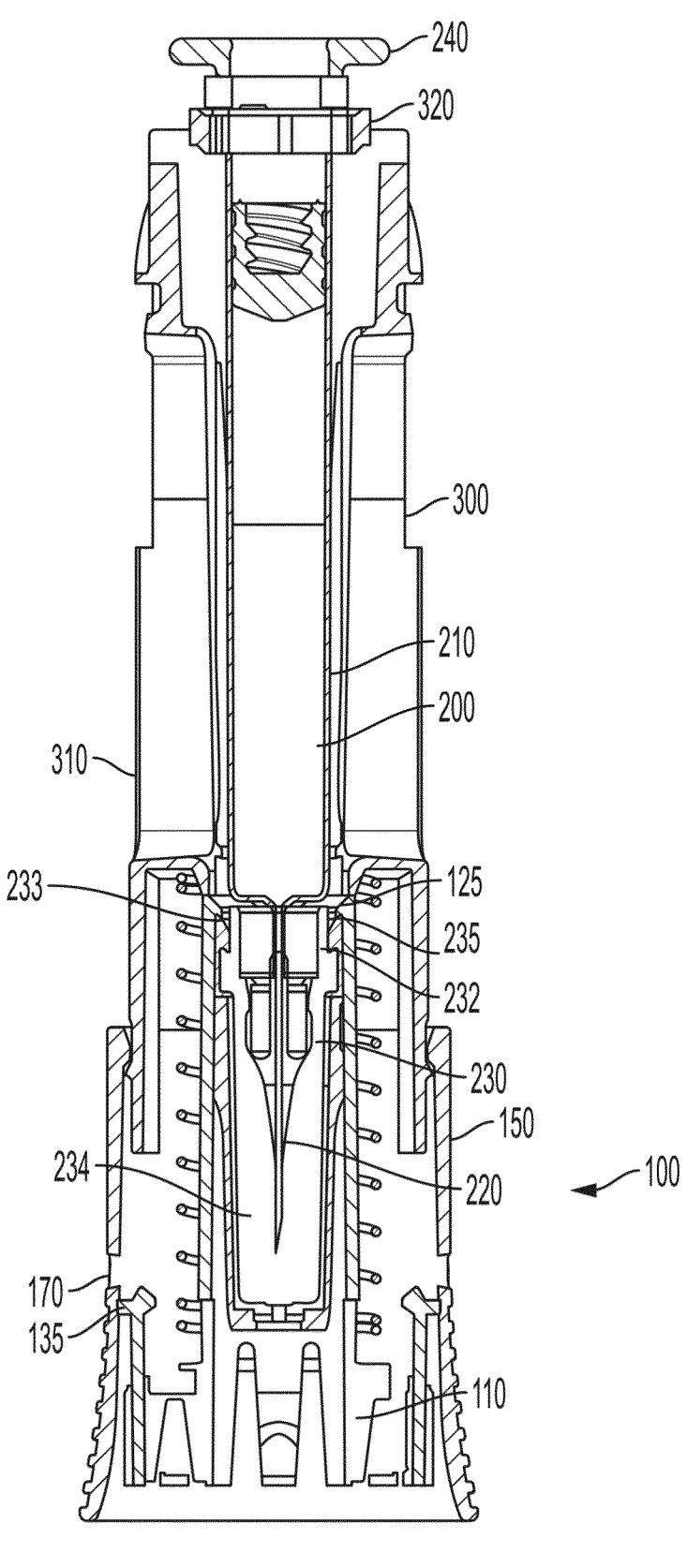
FIG. 8 is a cross-sectional view of an autoinjector including a cap assembly according to a non-limiting embodiment or aspect described herein.
Figure 9:
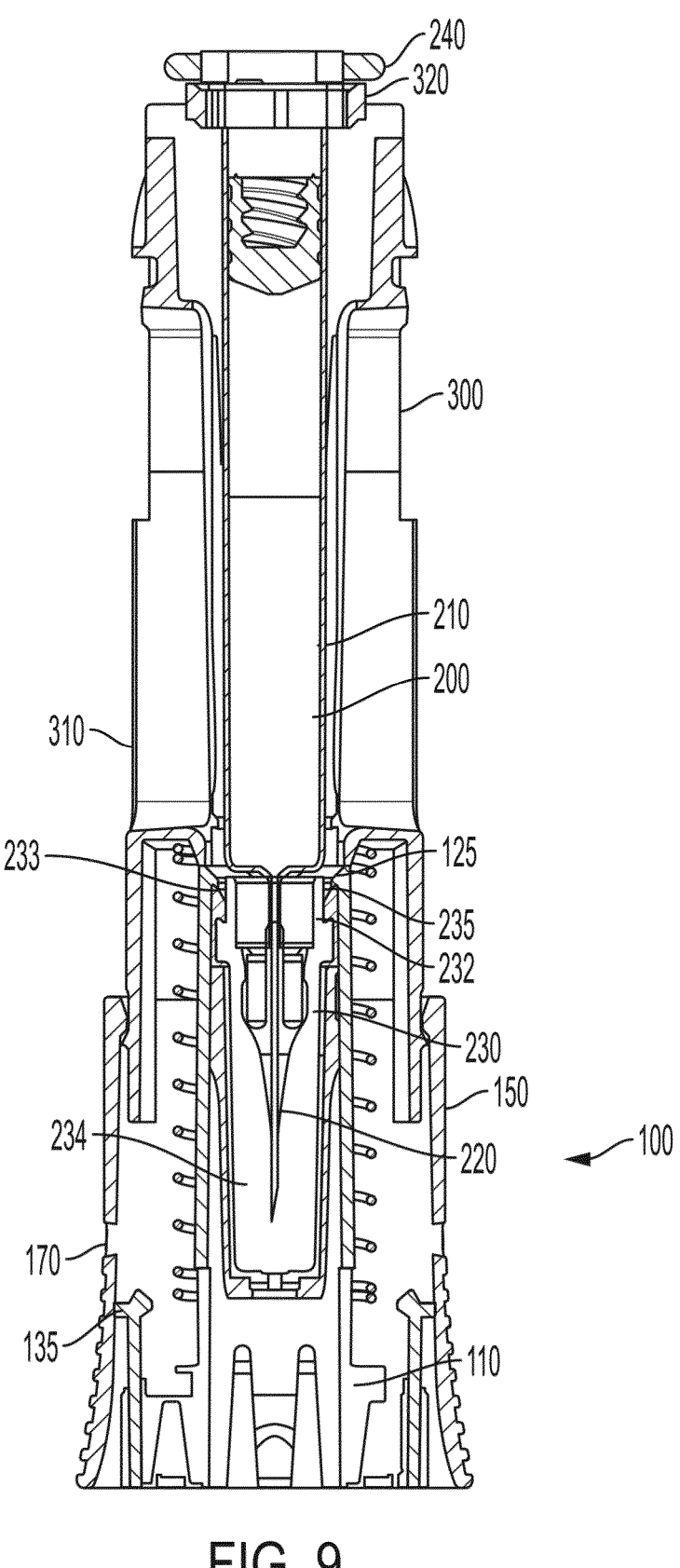
FIG. 9 is a cross-sectional view of an autoinjector including a cap assembly according to a non-limiting embodiment or aspect described herein.

Also provided herein is an autoinjector including a housing, a syringe having a barrel, a needle, and a needle shield, and a cap assembly. Turning to FIGS. 7-9, shown is an autoinjector having a housing, a syringe (200) having a barrel (210) and a needle (220) attached thereto, a removable needle shield (230) configured to at least partially surround the needle (220), and a cap assembly (100). The autoinjector housing (a lower housing (310) is shown, though it should be understood that autoinjector can include an upper housing, as described below) includes a proximal end and a distal end, where the distal end is open to permit the needle (220) to pass therethrough to allow a substance to be delivered to a user.

Removable needle shield (230) can include proximal (232) and distal (234) ends. In non-limiting embodiments or aspects, removable needle shield (230) is a two-piece needle shield, including an elastomeric inner portion and a rigid outer portion. In non-limiting embodiments or aspects, the rigid outer portion at least partially surrounds the elastomeric inner portion of the needle shield (230). In non-limiting embodiments or aspects, needle shield (230) includes at least one flange or shoulder (235). In non-limiting embodiments or aspects, the at least one flange or shoulder (235) is located on the elastomeric inner portion, for engaging the rigid outer portion. In non-limiting embodiments or aspects, needle shield (230) includes at least one complementary grasping feature (233) on the proximal end (232) thereof. In non-limiting embodiments or aspects, the at least one complementary grasping feature (233) is configured to be complementary to, and engageable with, the at least one grasping feature (125) of the retainer. In non-limiting embodiments or aspects, the at least one complementary grasping feature (233) is the proximal edge of the needle shield (230).

In non-limiting embodiments or aspects, the elastomeric portion of the needle shield (230) is formed of one or more natural or synthetic rubbers and/or of thermoplastic elastomer, or combinations thereof. In non-limiting embodiments or aspects, the rigid outer portion of the needle shield (230) is formed of a rigid plastic. In non-limiting embodiments or aspects, the rigid outer portion is formed of polypropylene.

Cap assembly (100) includes, as described previously, cap remover (150) and retainer (110). In non-limiting embodiments or aspects, the cap remover (150) and/or retainer (110) include one or more of the features described above. In non-limiting embodiments or aspects, cap remover (150) at least partially surrounds the open distal end of the housing.

In non-limiting embodiments or aspects, cap remover (150) is not rotatable relative to the housing. Autoinjector housing and/or cap remover (150) can include suitable features to prevent rotation of the cap remover (150), and, accordingly, retainer (110) and needle shield (230), relative to the housing and the needle (220), during needle shield (230) removal. In non-limiting embodiments or aspects, suitable anti-rotation features include one or more projections, guide channels, and/or shoulders on cap remover (150) and/or housing.

Also provided herein is a method of assembling an autoinjector including a cap assembly, including the steps of providing a lower housing assembly of an autoinjector, inserting a syringe into the lower assembly, and placing an upper assembly on the lower assembly. In a first step, a lower housing assembly (300), including cap assembly (100) engaged therewith, is provided. The lower housing assembly (300) includes lower housing (310). In non-limiting embodiments or aspects, lower assembly (300) includes a ring (320) at a proximal end thereof. The lower housing assembly (300) includes a proximal end and a distal end, the distal end being open to allow a needle of a syringe to pass therethrough, and the proximal end of the lower housing (310) being open to allow a syringe to be inserted into the housing. Housing may be formed of any suitable material, including, for example and without limitation, a rigid plastic. Lower assembly (300) also includes a cap assembly (100). Cap assembly (100) includes, as described previously, cap remover (150) and retainer (110), each having distal ends (160, 120) having an opening (162, 122) therethrough. In non-limiting embodiments or aspects, the cap remover (150) and/or retainer (110) include one or more of the features described above. In an initial configuration (e.g., when cap assembly (100) is positioned on lower housing (310)), the distal end (120) of the retainer (110) is spaced from the distal end (160) of the cap remover (150).

With reference to FIG. 7, in non-limiting embodiments or aspects, in a second step of the method, a syringe (200) is inserted into the lower housing (310). The syringe (200) can include a barrel (210) to hold a medicament or other substance therein, a needle (220) arranged at a distal end of the barrel (210), and a removable needle shield (230). Syringe (200), barrel (210), needle (220), and needle shield (230) can include one or more of the features described above. Syringe barrel (210) can be of any useful size, and can be formed of any useful material, such as glass or plastic. In non-limiting embodiments or aspects, syringe (200) is a unitary syringe, and the needle (220) is formed with the syringe barrel (210). In non-limiting embodiments or aspects, syringe barrel (210) is not formed with needle (220) therein and, instead, a needle hub (not shown) holds needle (220). Syringe needle (220) can be formed of any useful material, and can be of any suitable gauge. Needle shield (230) can be a one-piece needle shield formed of an elastomeric material, or a two-piece needle shield having an inner portion formed of an elastomeric material and an outer portion formed of a rigid material. The needle shield (230) at least partially surrounds the needle (220). In non-limiting embodiments or aspects, syringe (200) includes a flange (240) at a proximal end thereof. At the conclusion of the second step, the distal end (120) of the retainer (110) remains longitudinally spaced from the distal end (160) of the cap remover (150).

In non-limiting embodiments or aspects, the step of inserting the syringe (200) includes moving the syringe (200) towards the distal end of the housing (310), preferably such that the at least one grasping feature (125) is spaced longitudinally from the proximal end of the needle shield. In other words, the at least one grasping feature (125) is more proximal than in its final position (shown in FIG. 9). In this position, the distal end (234) of the syringe flange (240) abuts the ring (320). In this position, the proximal end (115) of the retainer (110) contacts the syringe barrel (210).

As described above, at the conclusion of this step, the distal end (120) of the retainer (110) is maintained proximally with respect to the distal end (160) of the cap remover (150), such that the distal end (120) of the retainer (110) is longitudinally spaced from the distal end (160) of the cap remover (150). In non-limiting embodiments or aspects, a tool (not shown) is inserted within the opening (162) of the cap remover (150). This tool can be used to push the retainer (110) proximally, such that the distal end (120) of the retainer (110) is longitudinally spaced from the distal end (160) of the cap remover (150).

In non-limiting embodiments or aspects, the proximal end (115) of the retainer (110) includes at least one grasping feature, such as projections (125), and the projections (125) contact the syringe barrel (210) proximally of the distal end of the syringe barrel (210). In this way, the retainer (110) is in an "overstroked" position, where the at least one grasping feature (125) is located too far proximally of the needle shield (230) (FIG. 7). In non-limiting embodiments or aspects, the needle shield (230) includes at least one flange or shoulder (235), and the proximal end (115) of the retainer (110) includes at least one grasping feature (125), and the at least one grasping feature (125) contacts the syringe barrel (210) proximally of the at least one flange or shoulder (235).

With reference to FIG. 8, in non-limiting embodiments or aspects, a third step of the method of assembling the syringe includes, after inserting the syringe (200) into the lower housing (310), moving the syringe (200) proximally. In non-limiting embodiments or aspects, moving the syringe (200) proximally within the lower housing (310) is achieved by inserting a device through the at least one opening (162, 122) in the distal ends (160, 120) of the cap remover (150) and retainer (110), and applying pressure to urge the syringe (200) proximally. In non-limiting embodiments or aspects, and as shown in FIG. 8, when the syringe (200) is urged proximally, the at least one grasping feature (125) of the retainer (110) engages the needle shield at a proximal-most end thereof. In non-limiting embodiments or aspects, the at least one grasping feature (125) engages at least one corresponding, complementary grasping feature (233) on the needle shield (230). In non-limiting embodiments or aspects, after the syringe (200) is urged proximally, the syringe flange (240) is longitudinally spaced from the ring (320) of the lower assembly (300). At the end of this step the at least one grasping feature (125) engages the at least one complementary grasping feature (233) of the needle shield (230), the distal end (120) of the retainer (110) is longitudinally spaced from the distal end (160) of the cap remover (150), and the syringe flange (240) is longitudinally spaced from the ring (320).

In non-limiting embodiments or aspects, the method includes a fourth step of placing an upper assembly (not shown), including an upper housing, on the lower assembly. As with lower assembly and lower housing, upper assembly and upper housing can be formed of any suitable material, including, for example and without limitation, a rigid plastic. In non-limiting embodiments or aspects, the step of placing the upper assembly on the lower assembly causes the syringe to move distally, such that the syringe flange (240) abuts the ring (320).

With reference to FIG. 9, after assembly, distal end (120) of retainer (110) falls or is otherwise displaced towards the distal end (160) of the cap remover (150), such that the distal end (120) of the retainer (110) abuts the distal end (160) of the cap remover (150).

Once a final user wants to remove the needle shield, he/she pulls the cap remover. As described above, the gap between the at least one protrusion (112) of the retainer (110) and the at least one shoulder (152) of the cap remover (150) causes a lag between the initiation of longitudinal movement of the cap remover (150) away from the lower housing assembly (300) and the initiation of longitudinal movement of the retainer (110) away from the lower housing assembly (300).

Figure 10:
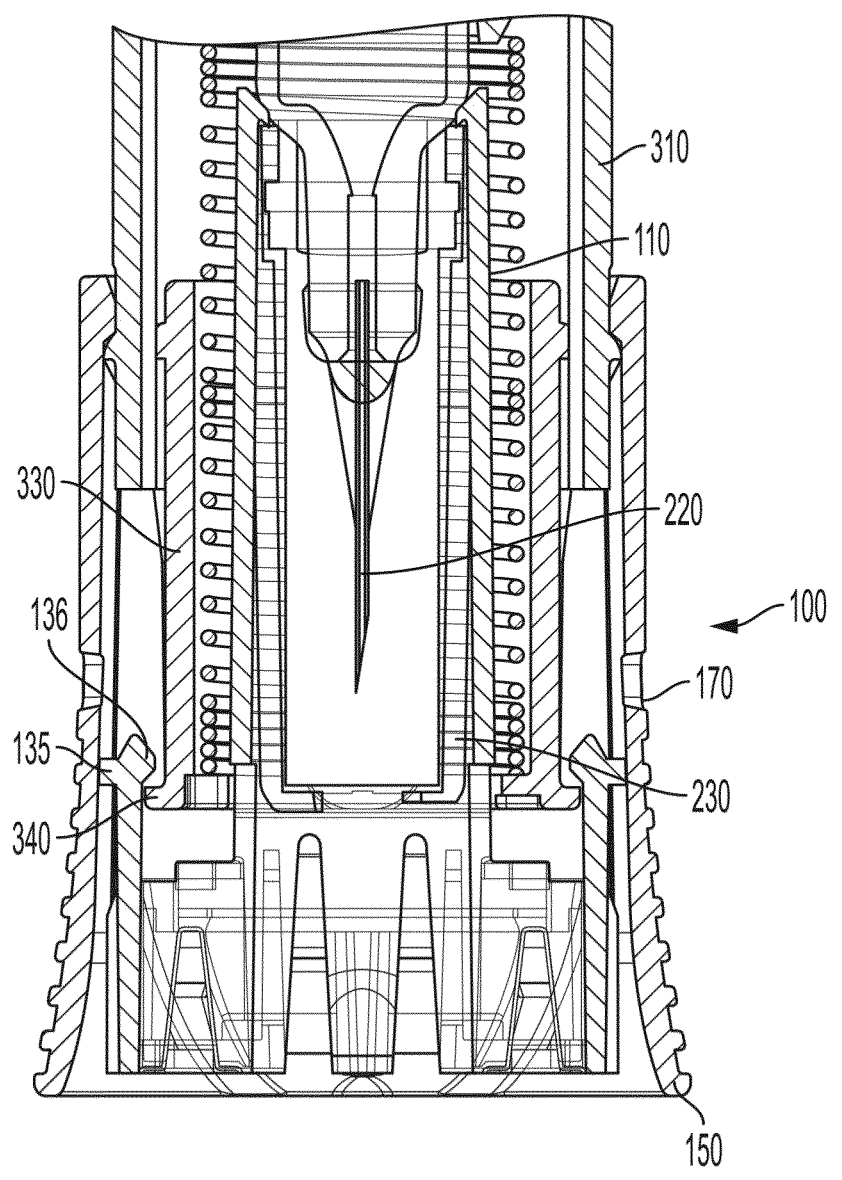
FIG. 10 is a cross-section view of a subassembly including a cap assembly according to a non-limiting embodiment or aspect described herein.

Turning to FIG. 10, in non-limiting embodiments or aspects, the cap assembly (100) functions to prevent actuation of a drug delivery device, such as an autoinjector, to which the cap assembly (100) is attached. With reference to FIG. 12, shown is one non-limiting embodiment or aspect of an autoinjector with which the present assembly can be utilized. Autoinjector (500) includes lower housing assembly or subassembly (300) as described previously, an upper housing subassembly (400), cap remover (150), and retainer (110). The lower subassembly includes housing (310) and a needle cover (330). In the non-limiting embodiments or aspects shown in FIGS. 10-12, needle cover (330) is configured to shield the needle (220) of the syringe (200) from a user when, for example, the removable needle shield (230) has been removed. Needle cover (330) is moveable from an extended position (pre-use), to a retracted position (use), where the needle cover (330) translates proximally into the lower housing assembly (300), to a second extended position (post-use). In both extended positions (pre- and post-use), the needle cover (330) at least partially shields the needle (220). In the use position, the needle cover (330) does not shield the needle, which can be inserted into a user's skin.

In the non-limiting embodiments or aspects shown in FIGS. 10-12, in order to use the autoinjector (500), a user removes the cap assembly (100) as described above (and below) and applies the distal end of the autoinjector (500) to the skin at the site of the intended injection. Needle cover (330) is positioned at the distal end of the autoinjector, and thus contacts the skin of the user. Application of force to the autoinjector (500) towards the skin causes movement of the needle cover (330) proximally into the housing (310) of the lower housing subassembly. In non-limiting embodiments or aspects, movement of the needle cover (330) proximally allows for delivery of the medicament, for example through interaction of the needle cover (330) with a container holder (not shown). Specifically, in non-limiting embodiments or aspects, proximal movement of the needle cover (330) causes the needle cover (330) to, at its proximal end (335), contact a container holder provided in the upper housing subassembly (400), which subsequently causes the container holder to be displaced proximally. The container holder can have at least one window (not shown) that allows biased blocking elements (not shown), which hold the plunger (not shown) of the autoinjector (500) in a pre-use position against the biasing force of an injection spring (not shown), to move radially to an unbiased position. The radial movement of the blocking elements releases the plunger, which is displaced out of the container holder by the injection spring, which moves a piston (not shown) in the syringe barrel (210) to cause injection of medicament through the needle (220).

As can be appreciated from the above-described embodiment or aspect, proximal movement of the needle cover (330) can cause unintended actuation of the autoinjector (500). Accordingly, as shown in FIGS. 10 and 11, in non-limiting embodiments or aspects provided is a subassembly for a drug delivery device, such as an autoinjector. The subassembly includes a housing (310), needle cover (330), and cap assembly (100) including retainer (110) and cap remover (150). In non-limiting embodiments or aspects, the retainer (110) prevents unintended proximal movement of the needle cover (330), and thus unintended actuation of a drug delivery device of which the subassembly is a component. In non-limiting embodiments or aspects, the retainer (110) includes at least one protrusion, such as inward-facing protrusion (136). In non-limiting embodiments or aspects, the at least one inward-facing protrusion (136) is arranged on the same proximally-extending arm on which at least one radially-extending protrusion (135) is positioned.

With continuing reference to FIGS. 10 and 11, in non-limiting embodiments or aspects, the needle cover (330) includes at its distal end a lip or flange (340), protruding outwardly. In non-limiting embodiments or aspects, inward-facing protrusion (136) on retainer (110) is located proximally of the lip or flange (340) of the needle cover (330), preventing the needle cover (330) from moving proximally a distance sufficient to allow actuation of the autoinjector (500). In non-limiting embodiments or aspects, inward-facing protrusion (136) engages or abuts the lip or flange (340) of the needle cover (330), substantially or completely preventing proximal movement of the needle cover (330).

FIG. 10 shows a non-limiting embodiment or aspect in which lip or flange (340) is arranged on an outer surface of needle cover (330), and protrusion (136) is an inward-facing protrusion configured to engage the lip or flange (340). In non-limiting embodiments or aspects (not shown), the protrusion is an outward-facing protrusion and is arranged on an arm that extends proximally from the distal end of the retainer (110) through an interior space defined by the needle cover (330), and is configured to engage a lip or flange arranged on an inner surface of the needle cover.

Turning to FIG. 11, shown is the aforementioned assembly process, with focus on the interaction between the at least one inward-facing protrusion (136) and the lip or flange (340) of the needle cover (330), and the at least one radially-extending protrusion (135) and the at least one opening (170).

Figure 11A:
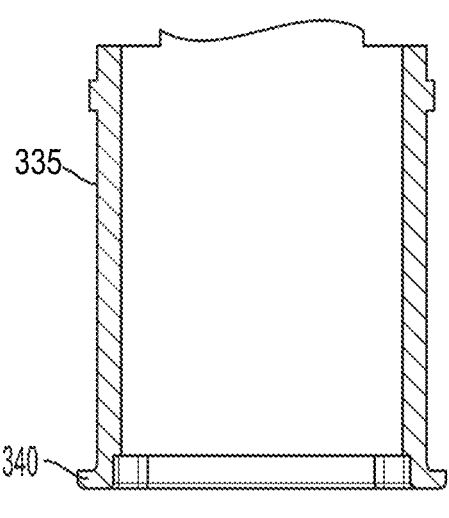
FIGS. 11A-11J show steps of assembly of a subassembly according to a non-limiting embodiment or aspect described herein.
Figure 11B:
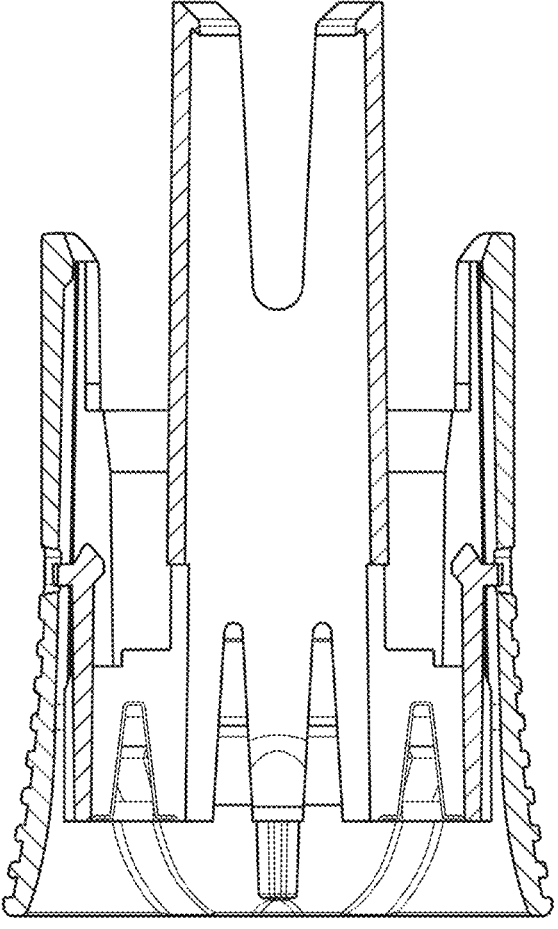
Figure 12:
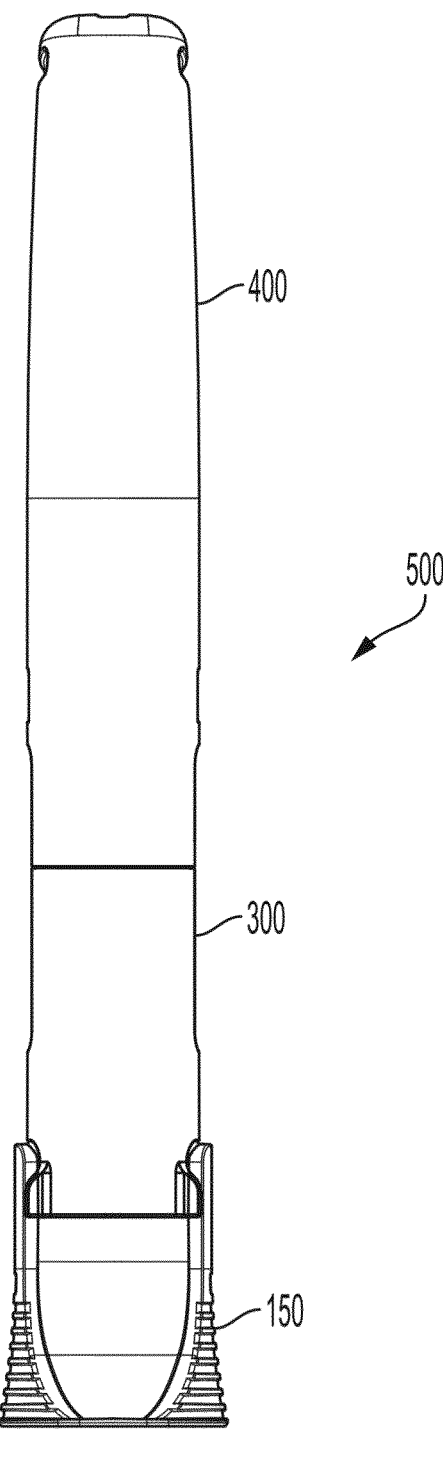
FIG. 12 shows a side view of an autoinjector according to a non-limiting embodiment or aspect described herein.

FIGS. 11A and 11B show needle cover (330) (graphically isolated from remainder of lower housing assembly (300)), having lip or flange (340), and cap assembly including cap remover and retainer, prior to placement of the needle cover into the cap assembly.

Figure 11C:
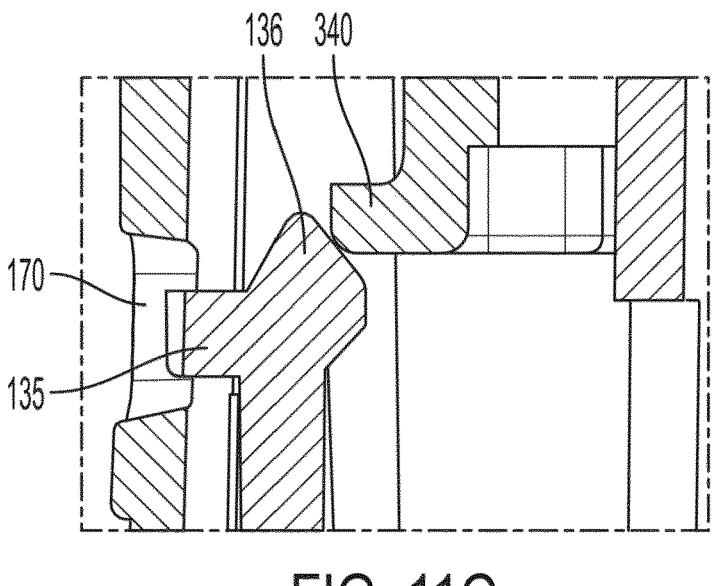
Figure 11D:
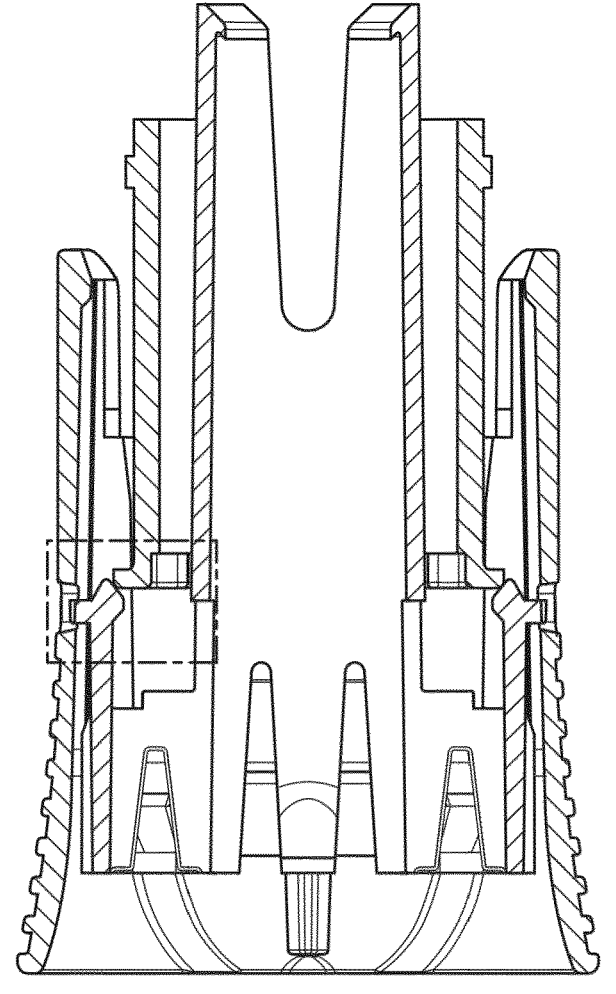

FIGS. 11C and 11D show an initial step of assembly, when the cap assembly is first placed on the needle cover. The at least one radially-extending protrusion (135) of the retainer is capable of deflecting outwardly due to its longitudinal positioning with regard to the at least one opening (170). Lip or flange (340) of the needle cover is engaged with a proximal-facing surface of the at least one inward-facing protrusion (136).

Figure 11E:
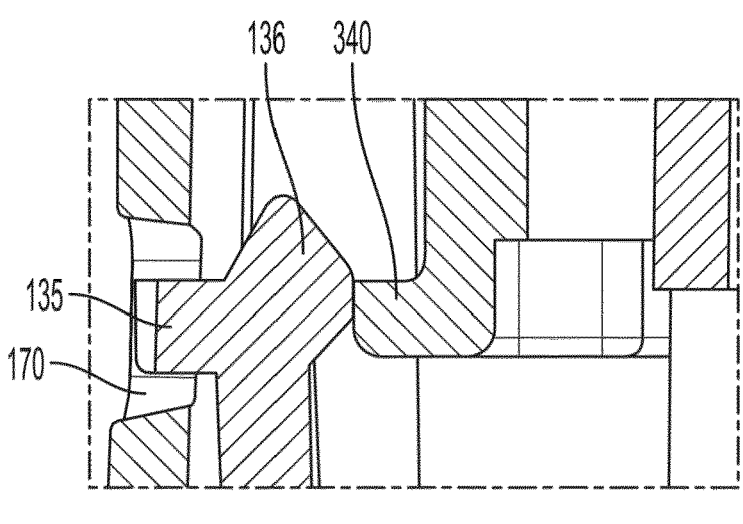
Figure 11F:
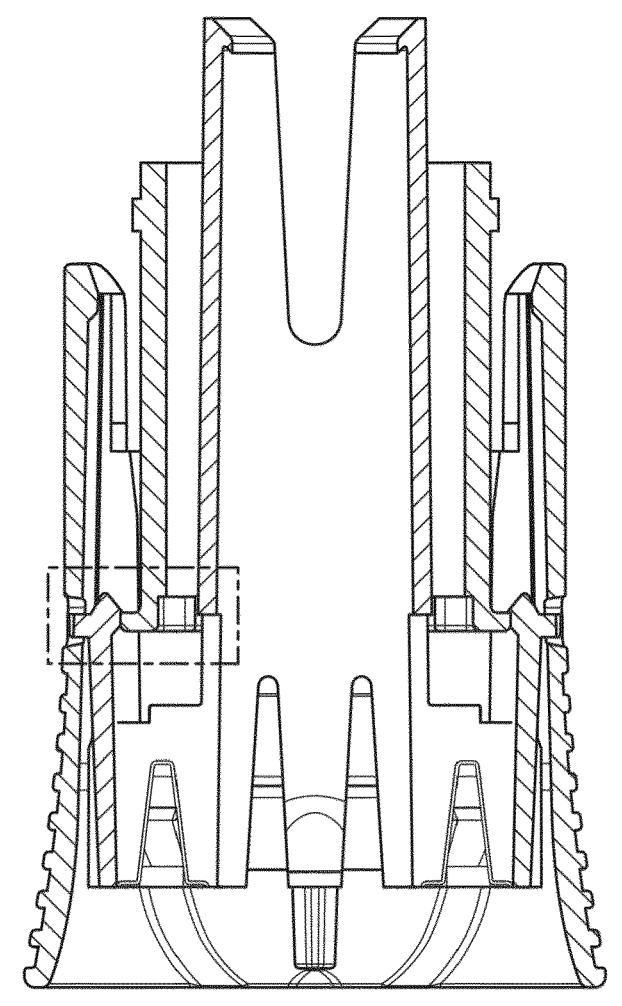

FIGS. 11E and 11F show a further step in the assembly process. Lip or flange (340) has begun to move distally past the at least one inward-facing protrusion (136). In non-limiting embodiments or aspects, where the at least one inward-facing protrusion (136) is positioned on at least one arm of the retainer, the arm(s) can flex outward as the lip or flange (340) passes by the at least one protrusion (136), allowing the needle cover to move distally past the protrusion(s) (136).

Figure 11G:
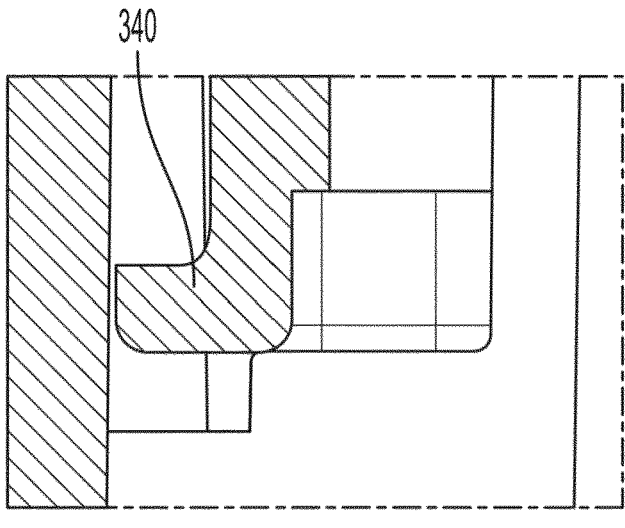
Figure 11H:
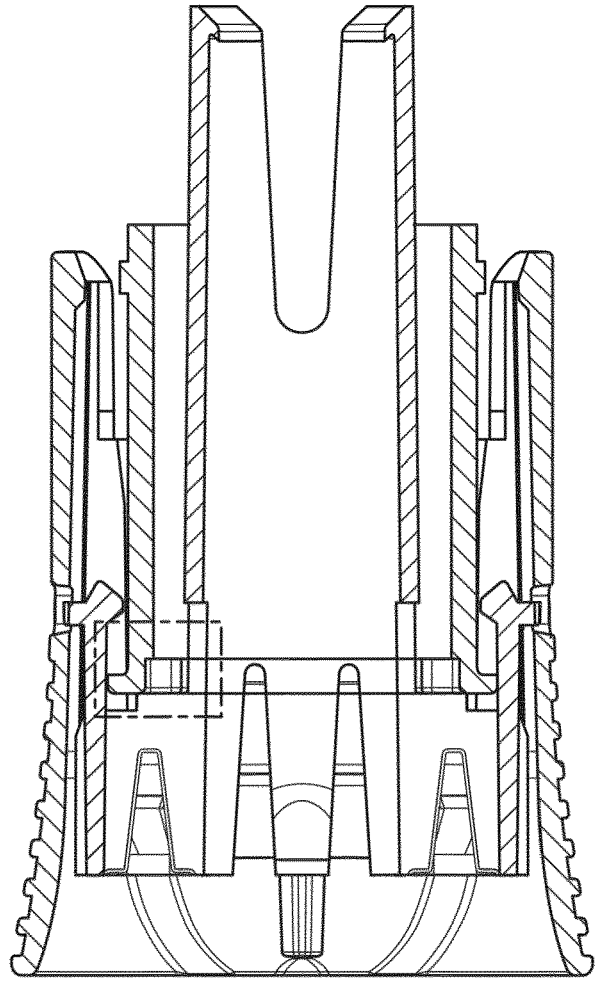

With continuing reference to FIG. 11, FIGS. 11G and 11H show a further step in the assembly process, where the lip or flange (340) has passed distally by the at least one inward-facing protrusion (136). In non-limiting embodiments or aspects in which the at least one inward-facing protrusion (136) can flex outward to allow lip or flange (340) to pass distally, the arm(s) have returned to an unbiased state.

Figure 11I:
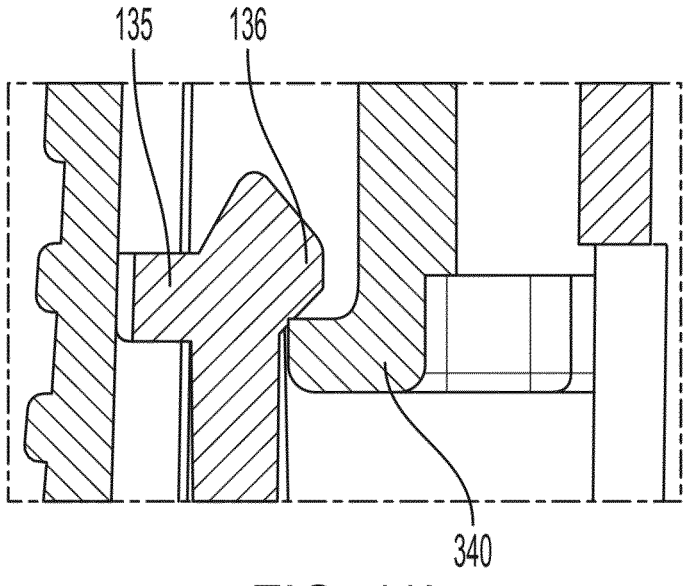
Figure 11J:
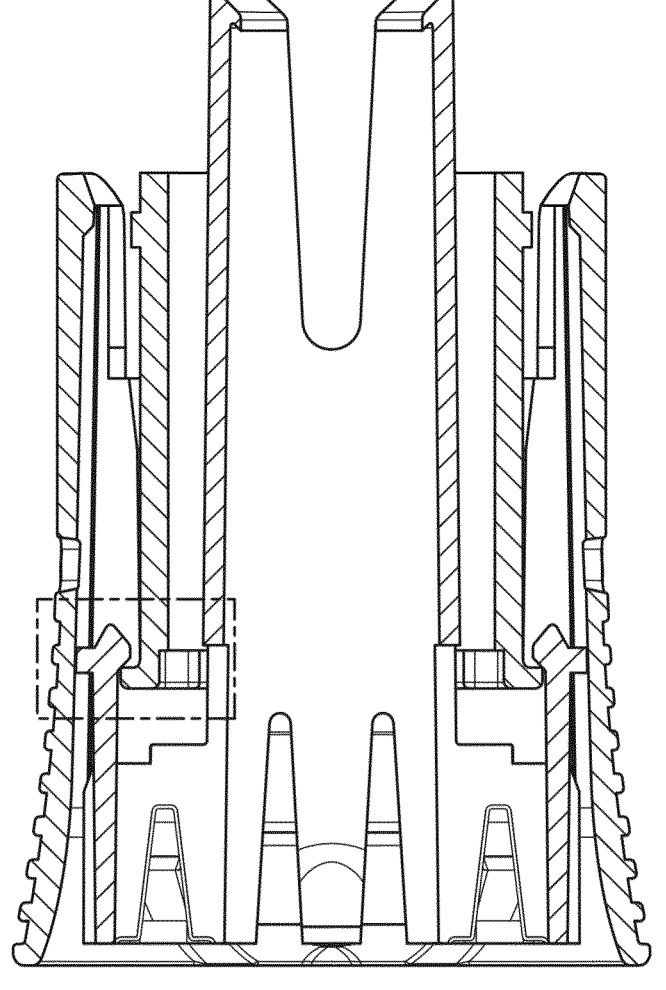

As described previously, after the lower housing (310) is assembled on the needle cover and cap assembly, the retainer moves distally (FIGS. 11I and 11J). By virtue of the arrangement of the assembly of the lower housing (310), the protrusions (135) are prevented from moving so that they are aligned with the openings (170). Consequently, the arms, including protrusions (135) are prevented from flexing outwardly as long as the cap assembly (100) is assembled on the lower housing assembly (300). The inward facing protrusions (136) are consequently maintained in engagement with the flange (340) of the needle cover (330). This engagement prevents proximal translation of the needle cover (330), which, as described above, prevents actuation of the auto-injector. In this way, unintended actuation of the device can be avoided.

To be able to use the autoinjector, the user has to first remove the cap assembly (100). To do so, he/she pulls the cap remover (150) away from the lower housing (310). Because of the axial "play" between the retainer (110) and the cap remover (150), the cap remover (150) will move with respect to the retainer (110), such that the at least one protrusion (135) is again aligned with the at least one opening (170), thereby allowing deflection of the arm of the retainer (110) outward and disengagement between the inward facing protrusion (136) and the flange (340) of the needle cover (330). This allows disengagement between the retainer (110) and the needle cover (330). The needle cover (330) is then free to move proximally to trigger an injection.

Although the invention has been described in detail for the purpose of illustration based on what is currently considered to be the most practical and preferred embodiments, it is to be understood that such detail is solely for that purpose and that the invention is not limited to the disclosed embodiments, but on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

The invention claimed is:

1. A subassembly for a drug delivery device comprising:
a housing;
a displaceable needle cover comprising a distal end comprising a flange, the needle cover received within the housing and configured to have a pre-use position in which the needle cover extends from the housing and a use position in which the needle cover is at least partially displaced into the housing, wherein displacement of the needle cover into the housing actuates the drug delivery device through interaction with a drive mechanism; and a cap assembly, comprising:
a cap remover configured to be grasped by a user; and
a retainer received within the cap remover, the retainer comprising at least one arm having at least one inward-facing protrusion on a first end of the arm, the at least one inward-facing protrusion arranged radially outward of and configured to engage the flange of the needle cover of the drug delivery device,
wherein the arrangement of the at least one inward-facing protrusion relative to the flange is configured to prevent movement of the needle cover to the use position,
wherein the retainer comprises at least one radially-extending protrusion located on the first end of the arm and extending in an opposite direction from the inward-facing protrusion and the cap remover comprises at least one opening extending through a sidewall thereof, wherein the at least one radially-extending protrusion is configured to deflect radially outward when the at least one radially-extending protrusion is aligned with the at least one opening in the cap remover; and
wherein the retainer is shiftable relative to the cap remover from a first position in which the at least one radially-extending protrusion is not aligned with the at least one opening in the cap remover and cannot deflect radially outward to a second position in which the at least one radially-extending protrusion is aligned with the at least one opening in the cap remover, such that the at least one radially-extending protrusion is capable of deflecting radially outward.

2. The subassembly of claim 1, wherein the flange is arranged on an outer surface of the needle cover.

3. The subassembly of claim 1, wherein the inward-facing protrusion abuts the flange on a proximal end thereof.

4. A drug delivery device comprising the subassembly for a drug delivery device of claim 1, further comprising a syringe comprising a needle and received at least partially within the housing, wherein in a use position the needle is positioned at least partially outside of the needle cover, wherein in the use position the needle cover is configured to actuate the drug delivery device to deliver a medicament.

* * * * *